(12) United States Patent
Fan et al.

(10) Patent No.: US 12,071,610 B2
(45) Date of Patent: Aug. 27, 2024

(54) APPARATUS AND METHOD FOR PERFORMING MICROORGANISM DETECTION

(71) Applicant: University of Florida Research Foundation, Inc., Gainesville, FL (US)

(72) Inventors: Zhonghui Hugh Fan, Gainesville, FL (US); Xiao Jiang, Gainesville, FL (US); Trevor B. Tilly, Gainesville, FL (US); John Lednicky, Gainesville, FL (US); Chang-Yu Wu, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 699 days.

(21) Appl. No.: 17/140,696

(22) Filed: Jan. 4, 2021

(65) Prior Publication Data
US 2021/0230533 A1 Jul. 29, 2021

Related U.S. Application Data

(63) Continuation-in-part of application No. PCT/US2019/044490, filed on Jul. 31, 2019.
(Continued)

(51) Int. Cl.
| | | |
|---|---|---|
| *C12M 1/34* | (2006.01) | |
| *B01L 3/00* | (2006.01) | |
| *C12M 1/36* | (2006.01) | |
| *C12M 3/00* | (2006.01) | |
| *G01N 33/569* | (2006.01) | |

(52) U.S. Cl.
CPC ............ *C12M 41/46* (2013.01); *B01L 3/527* (2013.01); *C12M 23/44* (2013.01); *C12M 41/48* (2013.01); *G01N 33/56916* (2013.01); *G01N 33/56983* (2013.01); *B01L 2200/025* (2013.01); *B01L 2200/026* (2013.01); *B01L 2200/028* (2013.01); *B01L 2400/0616* (2013.01)

(58) Field of Classification Search
None
See application file for complete search history.

(56) References Cited

U.S. PATENT DOCUMENTS

| | | | |
|---|---|---|---|
| 10,859,473 B2 | 12/2020 | Wu et al. | |
| 2010/0159577 A1* | 6/2010 | Tokumaru | C12M 41/48 435/289.1 |

(Continued)

OTHER PUBLICATIONS

ISR Mailed Dec. 8, 2022; International Patent Application PCT/US22/76456 Filed Sep. 15, 2022.
(Continued)

*Primary Examiner* — Samuel P Siefke
*Assistant Examiner* — Henry H Nguyen
(74) *Attorney, Agent, or Firm* — Thomas | Horstemeyer, LLP

(57) ABSTRACT

An apparatus and method are provided for performing detection of microorganisms (e.g., viruses) with high sensitivity. The apparatus and method are well suited for point-of-care (POC) testing in resource-limited regions and are capable of being operated with very little manual intervention and without the need for lab equipment. A variety of viruses can be detected with high sensitivity, including, for example, coronaviruses, Zika virus and flu viruses.

16 Claims, 17 Drawing Sheets
Specification includes a Sequence Listing.

Related U.S. Application Data

(60) Provisional application No. 62/712,571, filed on Jul. 31, 2018.

(56) References Cited

U.S. PATENT DOCUMENTS

| | | | |
|---|---|---|---|
| 2010/0285454 A1 | 11/2010 | You et al. | |
| 2010/0297754 A1 | 11/2010 | Solli et al. | |
| 2015/0308578 A1* | 10/2015 | Block, III | C12M 21/08 |
| | | | 137/625.48 |
| 2015/0328633 A1 | 11/2015 | Yoo | |
| 2016/0016166 A1 | 1/2016 | Rolland et al. | |
| 2016/0263577 A1 | 9/2016 | Ismagilov et al. | |
| 2016/0296927 A1 | 10/2016 | Kirschhoffer et al. | |
| 2018/0080570 A1 | 3/2018 | Block, III et al. | |
| 2020/0057085 A1 | 2/2020 | Wasson et al. | |
| 2021/0230533 A1 | 7/2021 | Fan et al. | |
| 2022/0023867 A1 | 1/2022 | Kedia et al. | |

OTHER PUBLICATIONS

Rowe, et al., "CareWatch: A Home Monitoring System for Use in Homes of Persons with Cognitive Impairment," Topics in Geriatric Rehabilitation, 2007, vol. 23, No. 1, pp. 3-8.

Rowe et al., "Reducing Dangerous Nighttime Events in Persons with Dementia by Using a Nighttime Monitoring System", Alzheimer's & Dementia 5, 2009, 419-426.

Spring et al., "Improving Caregivers' Well-Being by Using Technology to Manage Nighttime Activity in Persons with Dementia," Research in Gerontological Nursing, vol. 2, No. 1, 2009, pp. 39-48.

Bohl et al., "A Longitudinal Analysis of Total 3-Year Healthcare Costs for Older Adults who Experience a Fall Requiring Medical Care", JAGS, vol. 58, No. 5, May 2010.

International Search Report and Written Opinion dated Oct. 16, 2019 in copending PCT Application No. PCT/US2019/044490.

Jiang et al., Valve-enabled Sample Preparation and RNA Amplification in a Coffee Mug for Zika Virus Detection, Angewandte Chemie International Edition, Oct. 24, 2018.

ISR mailed Feb. 14, 2024 for International Patent Application PCT/US2023/080451, Filed Nov. 20, 2023.

Song, et al., "A lyophilized colorimetric RT-LAMP test kit for rapid, low-cost, at-home molecular testing of SARS-CoV-2 and other pathogens", Scientific Reports, vol. 12, Art 7046, Published Apr. 2022.

* cited by examiner

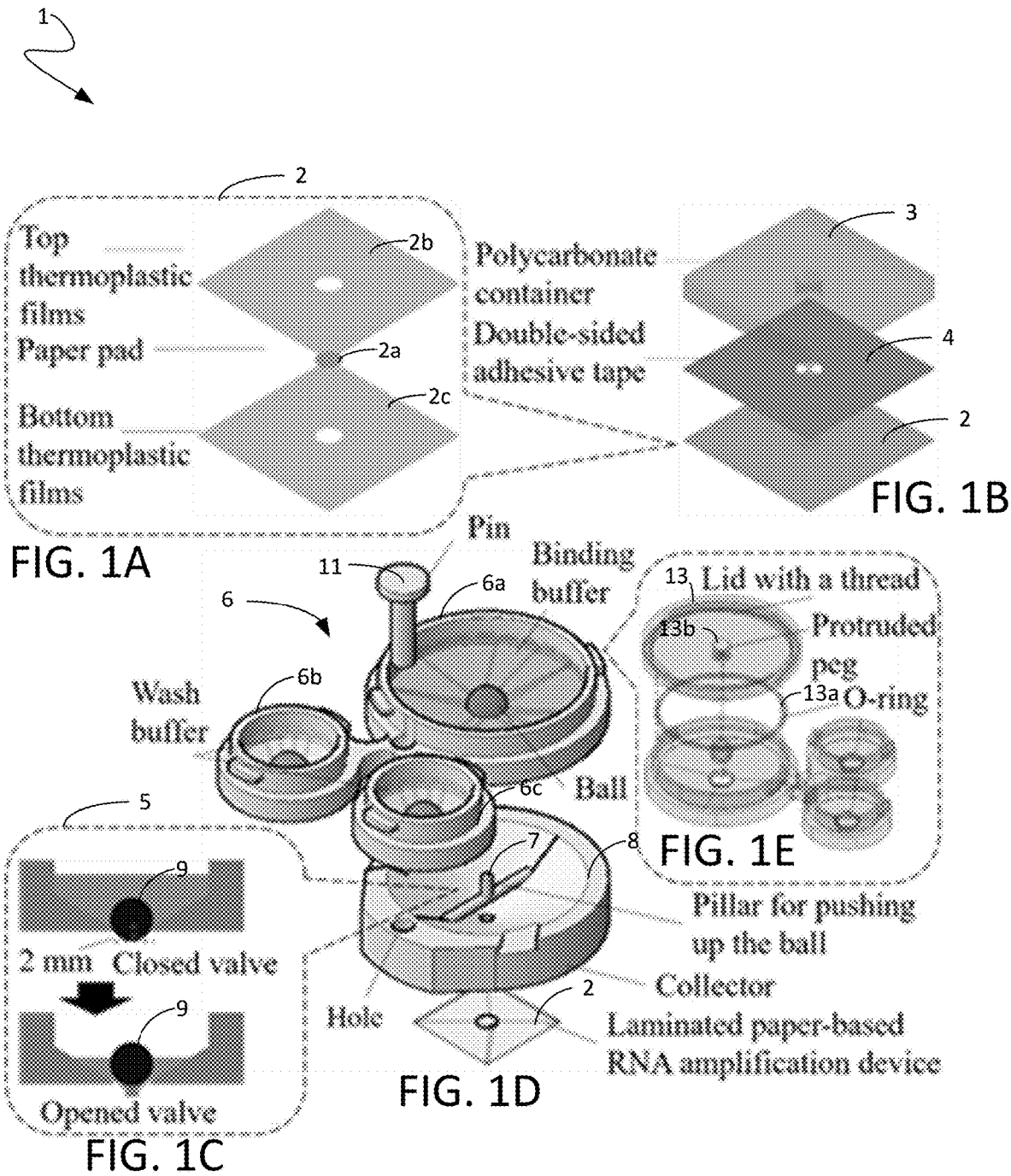

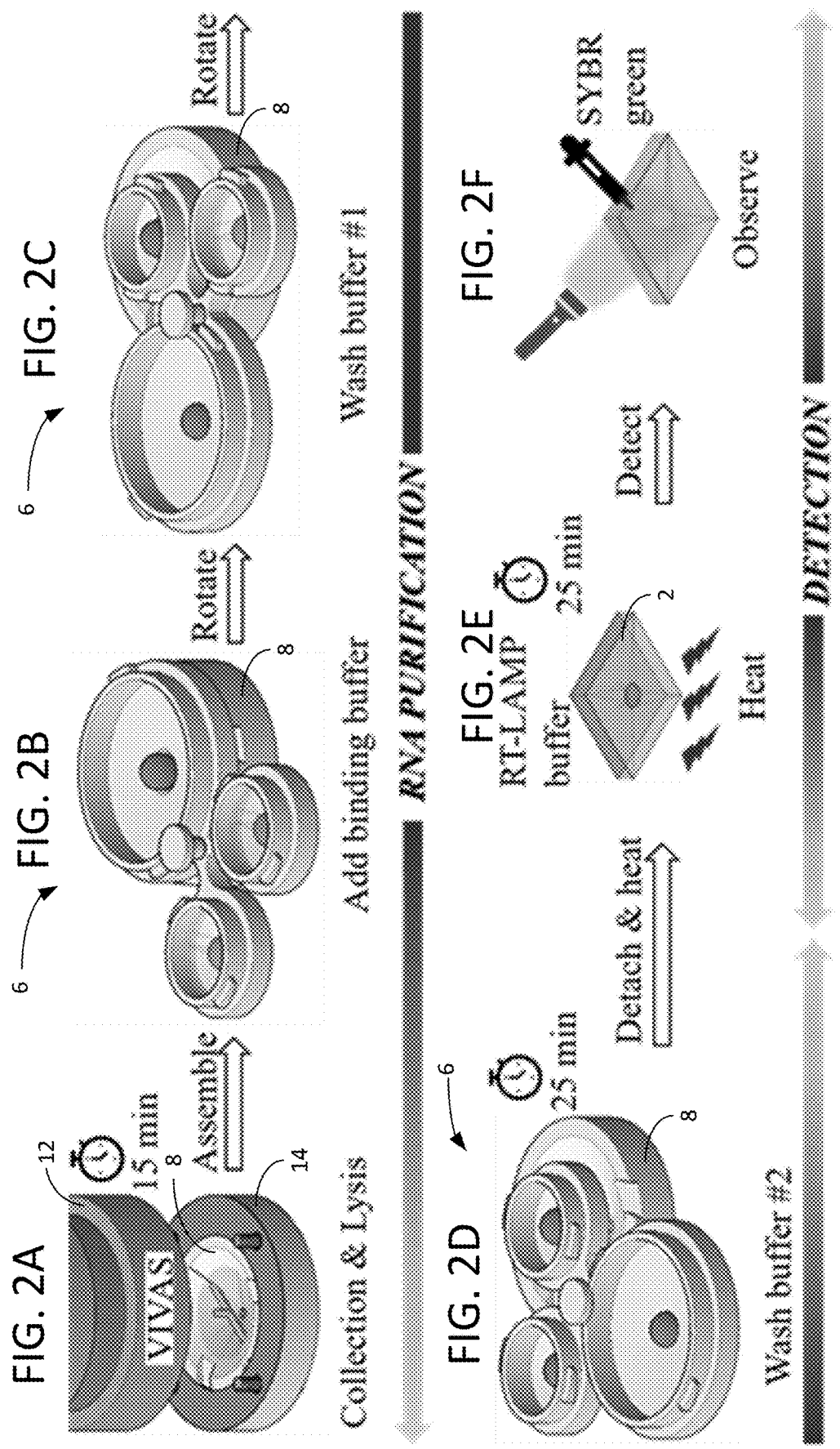

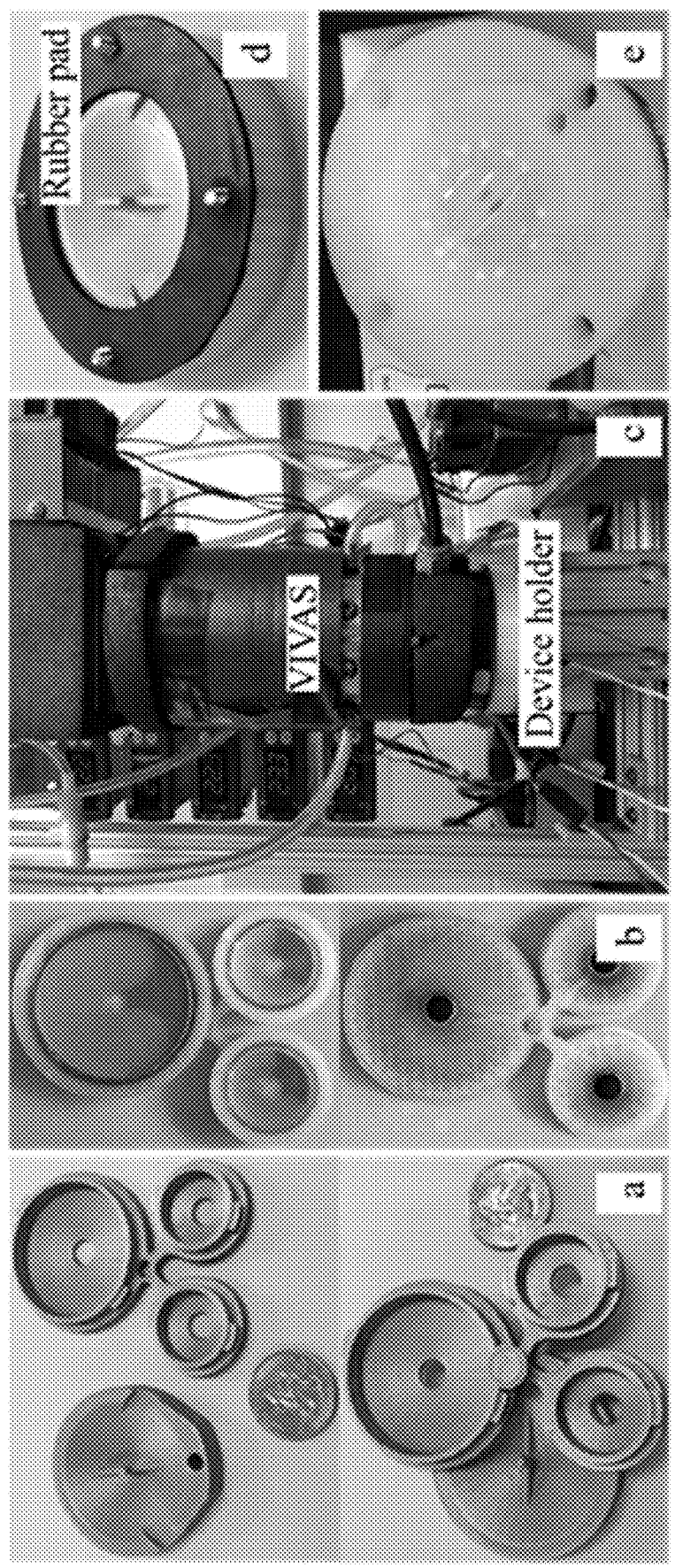

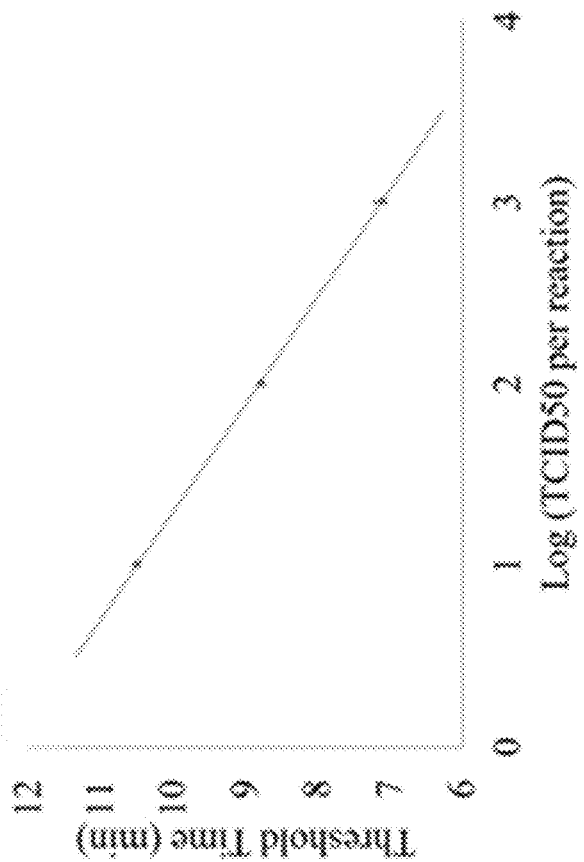
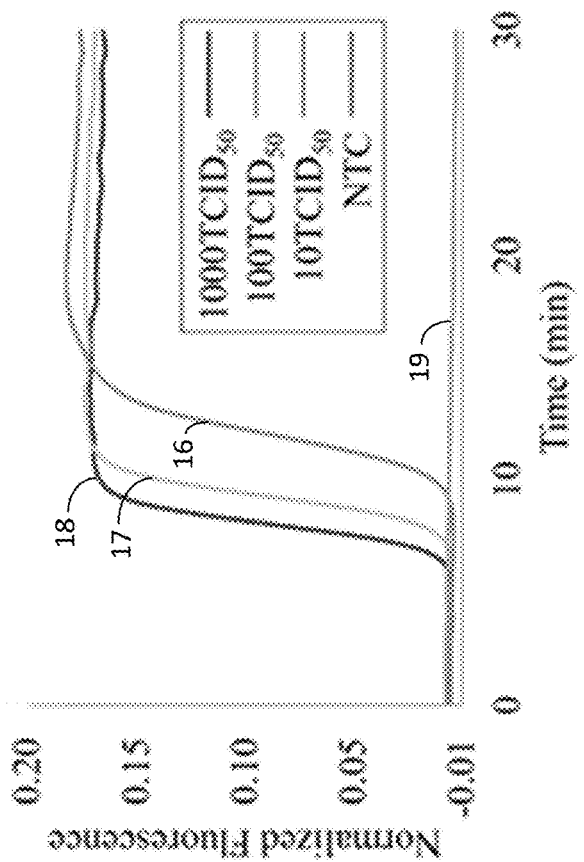
FIG. 4A
FIG. 4B

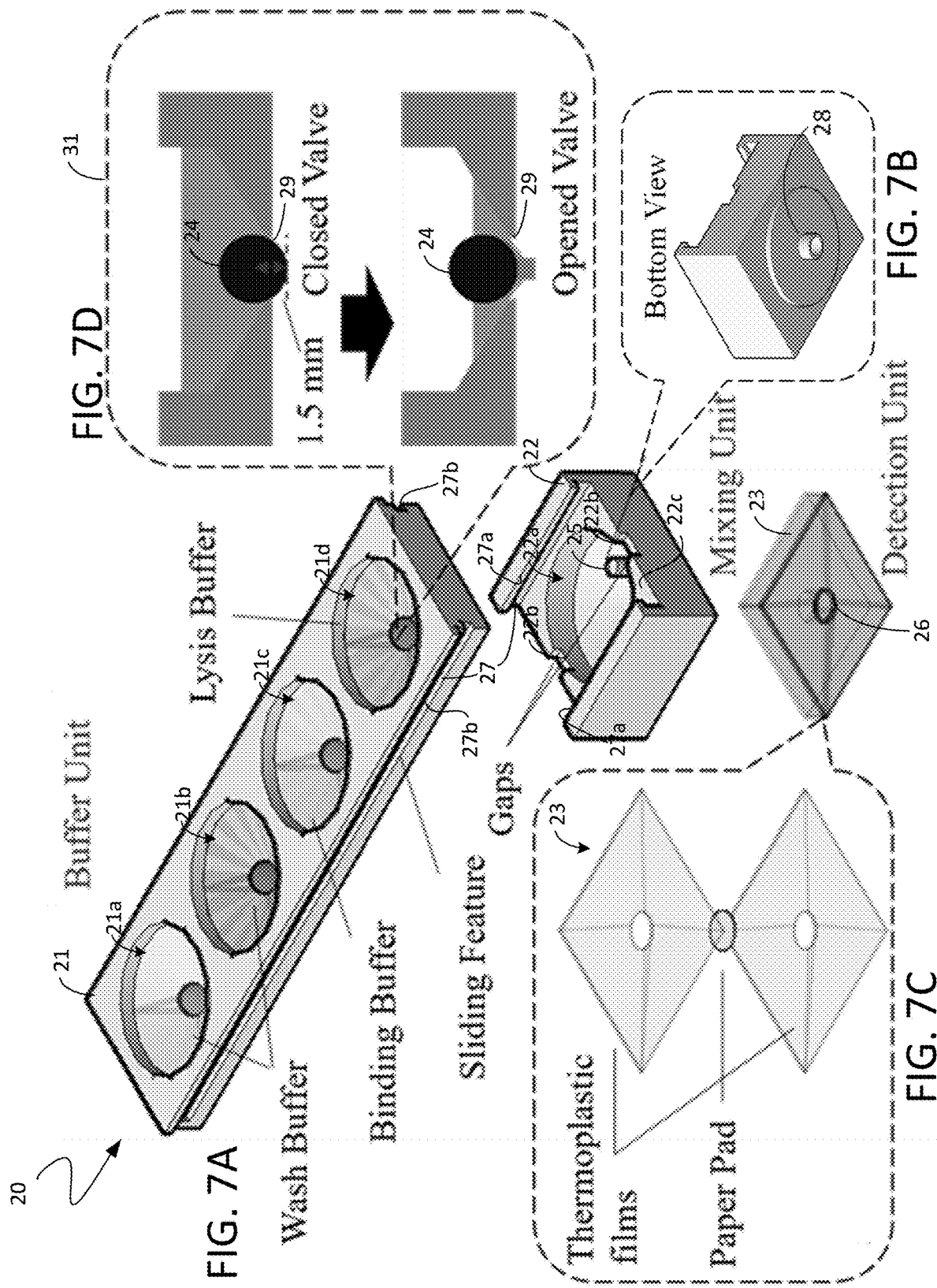

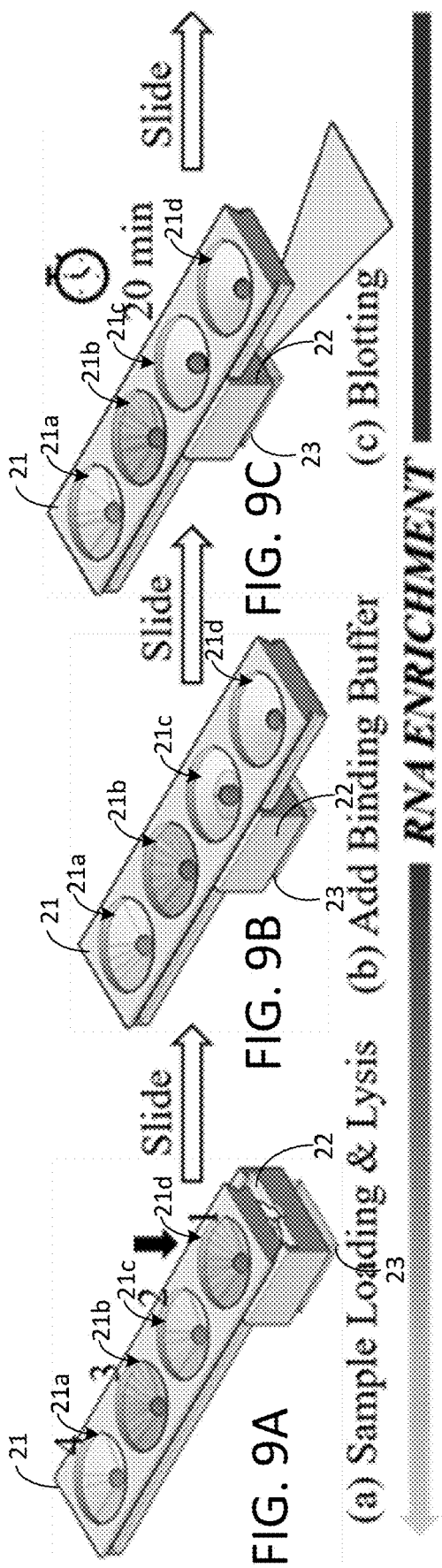
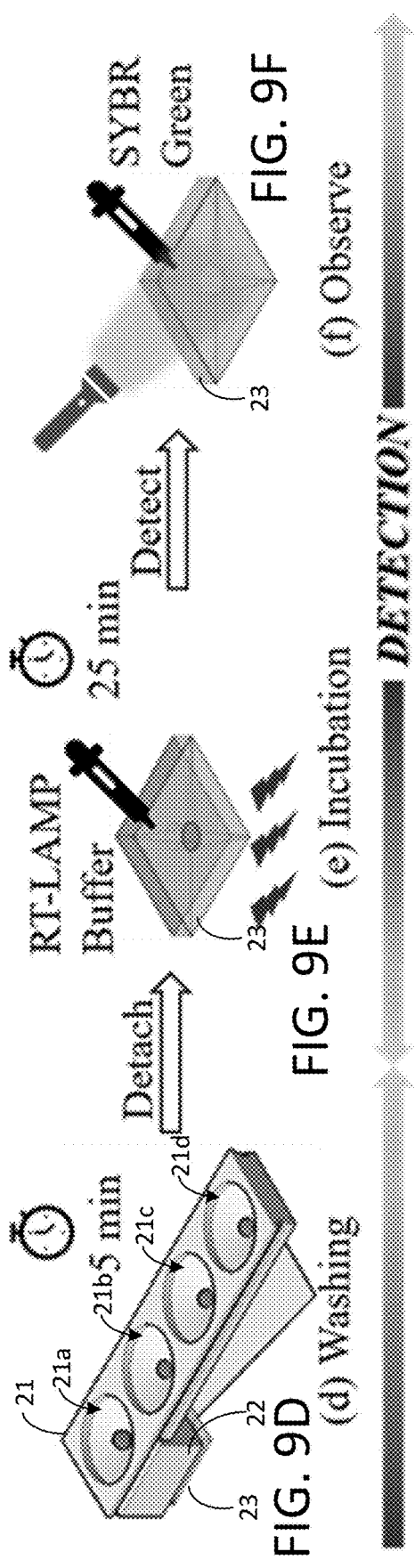

APPARATUS AND METHOD FOR PERFORMING MICROORGANISM DETECTION

CROSS-REFERENCE TO RELATED APPLICATIONS

This application is a continuation-in-part bypass application that claims priority to, and the benefit of the filing date of, PCT international application No. PCT/US2019/044490, filed on Jul. 31, 2019 and entitled "APPARATUS AND METHOD FOR PERFORMING MICROORGANISM DETECTION," which claims priority to, and the benefit of the filing date of, U.S. Provisional Application having Ser. No. 62/712,571, filed on Jul. 31, 2018 and entitled "APPARATUS AND METHOD FOR PERFORMING MICROORGANISM DETECTION," both of which are incorporated by reference herein in their entireties.

GOVERNMENT SUPPORT

This invention was made with government support under Grant No. 2030844 awarded by the National Science Foundation, and Grant No. 1353423 awarded by the National Science Foundation. The government has certain rights in the invention.

This invention was created in part by funding received from Grant No. 7ZK22 of the Zika Research Grant Initiative Project awarded by the Florida Department of Health, Biomedical Research Program, for The State of Florida.

CROSS-REFERENCE TO SEQUENCE LISTING

The genetic components described herein are referred to by sequence identifier numbers (SEQ ID NO). The SEQ ID NOs correspond numerically to the sequence identifiers <400>1, <400>2, etc. The sequence listing in written computer readable format (CRF) is submitted Apr. 19, 2021, as a text file named "222107-1315_Sequence_Listing_ST25.txt" created on Apr. 19, 2021, and has a size of 15,114 bytes.

TECHNICAL FIELD

This present disclosure relates to methods and apparatuses for detecting microorganisms.

BACKGROUND

The recent global outbreaks of Zika virus disease and its association with neurological complications represent a long-term public health challenge. Zika virus is a mosquito-borne flavivirus (family Flaviviridae) that caused epidemics in Brazil in 2015 and spread quickly into the United States. The Zika virus disease became a nationally notifiable condition in 2016. Zika virus was first isolated from a non-human primate in 1947 in Africa. Zika virus infections in humans were sporadic before the first outbreak in 2007 and thought to be mainly asymptomatic, some causing dengue-like symptoms such as fever, headache, rash, arthralgia, myalgia and conjunctivitis. Since the French Polynesian outbreak in 2013, however, Zika virus disease has been associated with severe neurological complications, including Guillain-Barre syndrome (GBS) in adults and microcephaly in neonates.

The modern international travel and dense population in cities greatly increase the ability of vector-borne diseases such as Zika to cause global epidemics. Moreover, developing countries where infectious diseases affect most people often lack well-equipped laboratories to conduct molecular diagnosis for viruses. As a result, it is vital to develop fast, reliable, portable and affordable diagnostic tools to monitor the emergence and the spread of Zika virus disease.

The U.S. Centers for Disease Control and Prevention (CDC) recommend Zika virus RNA nucleic acid testing (NAT) and Zika virus and/or dengue virus IgM testing for symptomatic patients with possible Zika exposure. In countries with limited laboratory resources to preform molecular diagnosis, serological testing by IgM and IgG enzyme-linked immunosorbent assay (ELISA) or lateral flow assay (LFA) is often performed for the rapid diagnosis of similar flavivirus infections. However, due to the high level of structural similarity between the envelop protein of Zika virus and that of other flaviviruses, poor-specificity and cross-reactivity have been observed for antibodies elicited by Zika virus infection. Moreover, the sensitivity of rapid immunosorbent assay such as LFA is largely affected by the affinity of the specific antibody used by the test. Therefore, NAT such as reverse transcription polymerase chain reaction (RT-PCR) or reverse transcription loop-mediated isothermal amplification (RT-LAMP) is highly recommended when detecting Zika virus infection, especially for developing a point-of-care (POC) test for resource-limited regions. For DNA viruses, NAT can be PCR or LAMP. For other microorganisms such as Escherichia coli (E. coli) bacteria, NAT is PCR or LAMP. LAMP or RT-LAMP can also be replaced with other isothermal application methods including rolling circle amplification (RCA), helicase-dependent amplification (HDA), recombinase polymerase amplification (RPA), nucleic acid sequence-based amplification (NASBA), and others.

RT-LAMP has been extensively used as a NAT for POC RNA virus detection system due to its robustness, high sensitivity and specificity, short incubation time, simplified thermal management and instrument-free product detection. Since the outbreak of Zika virus in 2013, a lot of RT-LAMP tests have been developed to specifically detect Zika virus RNA, some of which even have the ability to differentiate between Asian and African Zika linage.

Even though the robustness of RT-LAMP allows extraction-free virus sample to be used for amplification in some circumstances, the small sample volume and the dilution steps involved decrease the sensitivity of the test. Traditional RNA extraction methods such as the organic extraction method and the solid phase extraction (SPE) method are often time-consuming and labor-intensive. The requirement for centrifugation equipment, various kinds of reagents and a controlled environment often makes it unrealistic for most circumstances outside of a lab. As a result, many microfluidic NAT devices have been developed for POC testing employing the SPE technique, incorporating elements such as silicon micropillars, silica monolith, $SiO_2$ coating, packed silica beads and paramagnetic silica particles in microchannels. These devices, however, are expensive to make and often require lab instruments (e.g. syringe pump) to operate.

Airborne infectious reagents, such as influenza viruses, coronaviruses, rhinoviruses and adenoviruses, can be transmitted through three primary routes: (a) inhalation of pathogen-containing aerosols, (b) droplet infection, and (c) contact transmission. Understanding the aerosol transmission mode is of great importance, as the risk of respiratory disease transmission through this route is exceptionally high in population-dense areas, such as schools, hospitals, airports and industrial animal farms. However, the relative importance of the aerosol transmission route among the three is controversial, due to the limitations in the sampling and detection methods available for small-sized virus aerosols. Moreover, traditional methods used to detect the collected virus aerosols, for example, viral culture and polymerase chain reactions (PCR), are time-consuming and labor-intensive. The requirements of well-equipped lab and highly-trained personnel often make it unrealistic in resource-limited settings.

Compared to the great progress made to detect infecting agents present in other types of samples, such as aqueous samples, airborne pathogen detection is still a challenge and especially lacking in automated platforms with realistic and efficient sampling procedures. Due to the low pathogen content in aerosols, a huge volume of aerosols needs to be concentrated into a sub-milliliter-sized liquid typically used by biosensors to be detectable. The assignee of the present application has developed a Viable Virus Aerosol Sampler (VIVAS) as an efficient collector for the lab-generated, sub-micron-sized virus aerosols. The VIVAS is a laminar-flow, water-based condensational growth system capable of collecting aerosolized particles from 8 nm to 10 µm. The VIVAS has been successfully used to collect a variety of viable human respiratory viruses in a student infirmary of the University of Florida during a late-onset 2016 influenza virus outbreak as well as coronavirus disease 2019 (COVID-19). The high collection efficiency with the proven ability to collect real-world virus aerosols makes the VIVAS highly suitable for becoming a part of sample-to-answer virus aerosol detector.

An ideal sample-to-answer virus aerosol detection system includes an efficient aerosols collector and a rapid, sensitive detector for the collected virus. Moreover, these two components should be integrated in a way to operate without manual steps or with the minimum amount of manual interventions. Rapid enzyme immunoassay-based POC testing for human respiratory diseases such as the QuickVue Influenza A+B Test has been available in hospitals for serval years. However, the enzyme immunoassay-based POC testing has lower sensitivities compared to NAT.

Accordingly, a need exists for an improved method and apparatus for performing virus detection that can be operated with very little manual intervention, with high sensitivity, without the need for lab equipment, and that is suitable for POC testing in resource-limited regions.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention.

Moreover, in the drawings, like reference numerals designate corresponding parts throughout the several views.

FIGS. 1A-1E illustrates various aspects of the apparatus for detecting microorganisms in accordance with a representative embodiment.

FIGS. 2A-2F illustrate the method for detecting microorganisms using the apparatus shown in FIGS. 1A-1E.

FIGS. 3A-3E show photographs of the apparatus shown in FIGS. 1A-1E and the VIVAS that is used to collect the sample.

FIG. 4A is a graph showing curves representing normalized fluorescent signals of 10, 100, and 1000 $TCID_{50}$ H1N1 flu virus genome equivalents as a function of RT-LAMP time; the curves indicate that all samples' amplification signals reached the plateau in 20 minutes.

FIG. 4B is a standard curve (log $TCID_{50}$ per reaction vs. threshold time) generated with three replicates of each serial diluted H1N1 flu virus RNA samples.

FIGS. 7A-7D are perspective views of the apparatus and components thereof in accordance with another representative embodiment.

FIGS. 9A-9F illustrate the method for detecting microorganisms using the apparatus shown in FIGS. 7A-7D.

Figures 5A, 5B, 5C:
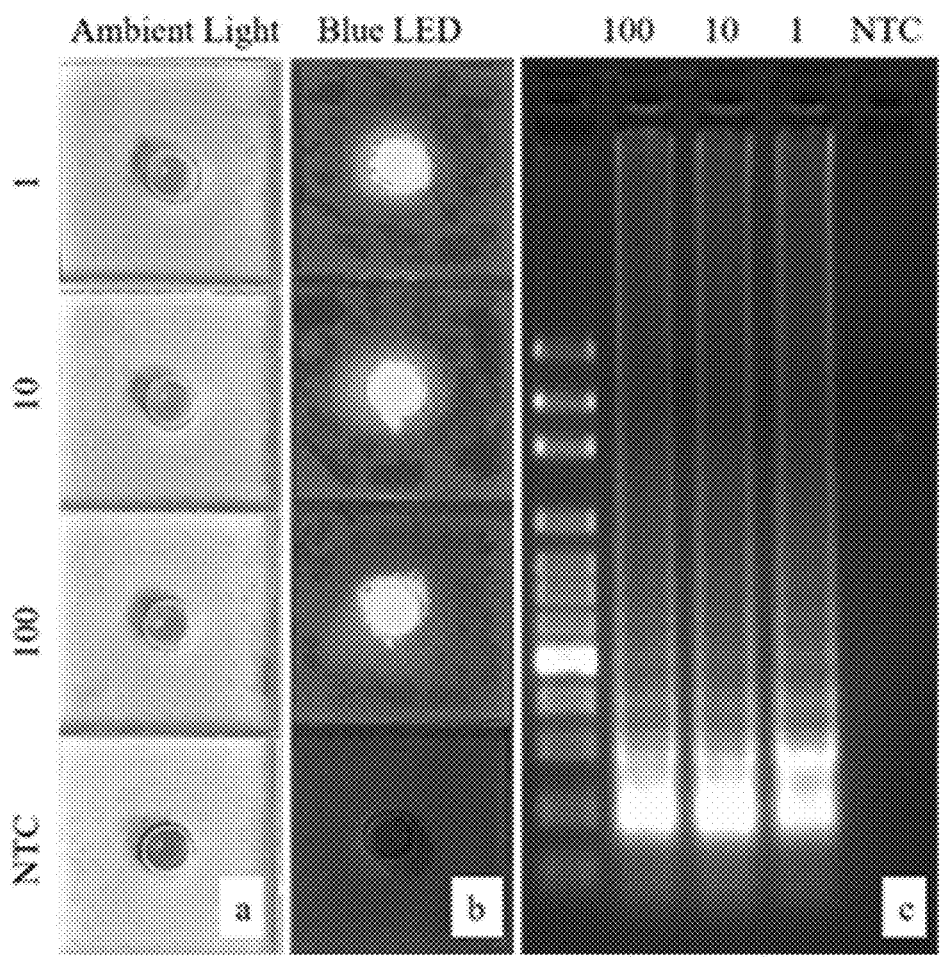
FIGS. 5A-5C are photographs showing how 1 $TCID_{50}$ H1N1 flu virus per 140 µL sample was successfully detected in one hour using the apparatus shown in FIGS. 1A-1E.

for 25 min for results obtained using the method and apparatus described with reference to FIGS. 7A-7C.

DETAILED DESCRIPTION

The present disclosure discloses an apparatus and a method for performing microorganism detection. The apparatus is capable of detecting microorganisms (e.g., viruses) with high sensitivity, is well suited for POC testing in resource-limited regions and is capable of being operated with very little manual intervention and without the need for lab equipment. A collector unit of the apparatus comprises at least a first reservoir for holding at least a first liquid sample. A buffer unit of the apparatus includes at least second, third and fourth reservoirs for holding at least second, third and fourth liquids, respectively. A mechanical coupling mechanism of the apparatus couples the collector unit and the buffer unit together in a manner that allows a user to create relative movement between the collector unit and the buffer unit by exerting a force on at least one of the buffer unit and the collector unit. A valve mechanism of the apparatus causes the second, third and fourth liquids to be released from the second, third and fourth reservoirs, respectively, into the first reservoir, in turn, when the user creates relative movement between the collector unit and the buffer unit to cause the second, third and fourth reservoirs to come into temporary alignment with the first reservoir for respective time periods. A detection unit of the apparatus that is removably coupled to the collector unit receives liquid from the first reservoir. The detection unit can be removed from the collector unit and analyzed to determine whether the liquid received by the detection unit contains a particular microorganism.

In the following detailed description, for purposes of explanation and not limitation, exemplary, or representative, embodiments disclosing specific details are set forth in order to provide a thorough understanding of the inventive principles and concepts. However, it will be apparent to one of ordinary skill in the art having the benefit of the present disclosure that other embodiments according to the present teachings that are not explicitly described or shown herein are within the scope of the appended claims. Moreover, descriptions of well-known apparatuses and methods may be omitted so as not to obscure the description of the exemplary embodiments. Such methods and apparatuses are clearly within the scope of the present teachings, as will be understood by those of skill in the art. It should also be understood that the word "example," as used herein, is intended to be non-exclusionary and non-limiting in nature.

The terminology used herein is for purposes of describing particular embodiments only, and is not intended to be limiting. The defined terms are in addition to the technical, scientific, or ordinary meanings of the defined terms as commonly understood and accepted in the relevant context.

The terms "a," "an" and "the" include both singular and plural referents, unless the context clearly dictates otherwise. Thus, for example, "a device" includes one device and plural devices. The terms "substantial" or "substantially" mean to within acceptable limits or degrees acceptable to those of skill in the art. For example, the term "substantially parallel to" means that a structure or device may not be made perfectly parallel to some other structure or device due to tolerances or imperfections in the process by which the structures or devices are made. The term "approximately" means to within an acceptable limit or amount to one of ordinary skill in the art. Relative terms, such as "over," "above," "below," "top," "bottom," "upper" and "lower" may be used to describe the various elements' relationships to one another, as illustrated in the accompanying drawings. These relative terms are intended to encompass different orientations of the device and/or elements in addition to the orientation depicted in the drawings. For example, if the device were inverted with respect to the view in the drawings, an element described as "above" another element, for example, would now be below that element.

Relative terms may be used to describe the various elements' relationships to one another, as illustrated in the accompanying drawings. These relative terms are intended to encompass different orientations of the device and/or elements in addition to the orientation depicted in the drawings.

The term "microorganism" or "microbe," as used herein, refers to a small (often, but not always, microscopic) organism that is typically, but not exclusively, single cellular, and includes organisms from the kingdoms bacteria, archaea, protozoa, and fungi. Viruses are also classified as microorganisms in the present disclosure document even though they are not living organisms by themselves.

The apparatus and method will first be described with reference to a representative embodiment for performing airborne virus detection in an example application in which the virus being detected is influenza. The apparatus and method will then be described with reference to a representative embodiment for detecting non-airborne viruses in an example application in which the virus being detected is the Zika virus. Data is also disclosed herein of experiments that were conducted using the method and apparatus to detect coronaviruses, and in particular, SARS-CoV-2. All of the representative embodiments described herein are capable of being implemented as portable, rapid, reliable and cost-effective diagnostic POC tools that can be operated without the need for lab equipment and with very little human intervention. Accordingly, the apparatuses and methods are well suited for, but not limited to, use in resource-limited regions.

The aerosol transmission route is one of the three major transmission routes of airborne infectious diseases. However, the dynamics and significance of the aerosol transmission route are not well understood, nor does there exist an automatic, efficient and realistic biosensor for detecting small-sized virus aerosols. As discussed above, the assignee's VIVAS is a water-vapor-based condensational growth system capable of collecting aerosolized particles (e.g., from 8 nm to 10 μm in size). In accordance with a representative embodiment described herein, the apparatus includes 3D-printed sample preparation components and a laminated paper-based RNA amplification component, referred to hereinafter collectively as the "SPRA" apparatus. In accordance with the representative embodiment, the SPRA apparatus is designed to integrate with the VIVAS to perform a rapid, sample-to-answer virus aerosol detection based on the RT-LAMP. The integrated SPRA apparatus and VIVAS is referred to hereinafter as the "integrated SPRA-VIVAS platform."

The 3D-printed sample preparation component of the SPRA apparatus includes an innovative "bearing ball valve" capable of storing and delivering reagents without manually pipetting. The inventors have tested the sensitivity of the SPRA apparatus to detect 1 $TCID_{50}$ H1N1 flu viruses spiked in 140 μL aqueous sample, which is more sensitive than the commercial FTA® card and Whatman™ glass microfiber. Using the integrated SPRA-VIVAS platform, the inventors have demonstrated the successful detection of lab-generated H1N1 flu virus aerosols in less than one hour. The results demonstrate that the SPRA-VIVAS platform has a great potential in airborne infectious disease screening and monitoring during outbreaks. The effective sampling and rapid detection of virus aerosols also facilitates a better understanding of the significance of aerosol transmission mode in airborne infectious disease outbreaks.

As indicated above, in accordance with a representative embodiment, the RT-LAMP is integrated with the VIVAS, with the RT-LAMP being used to detect the virus aerosols that are collected by the VIVAS. The RT-LAMP is an isothermal DNA amplification technique with high robustness, sensitivity and specificity. With its short incubation time and simplified thermal management, RT-LAMP can be easily employed by POC platforms. For RNA extraction from the collected virus aerosols, in accordance with a representative embodiment, a laminated paper-based device is used for extraction. Compared to analytical devices made of other materials, paper-based devices have the advantages of being extremely low-cost, flexible, easy to dispose and capable of pumping liquid using capillary forces. In accordance with an embodiment, 3D-printed components are used to house the laminated paper-based device and the RNA extraction reagents. In accordance with a representative embodiment, an innovative valving mechanism inspired by the small animal water bottle is employed to conduct RNA extraction without the help of even basic lab equipment such as a pipette. The 3D-printed components allow the laminated paper-based device to be combined with the VIVAS, so that the aerosols collected by the VIVAS can be directly impinged onto the RNA extraction pad.

FIGS. 1A-1E illustrate top perspective views of the SPRA apparatus 1 in accordance with a representative embodiment in its partially-disassembled state to reveal features of the various components of the SPRA apparatus 1 that would not be visible in the fully-assembled state. FIG. 1A shows the detection unit 2, which, in accordance with this representative embodiment, is a laminated paper-based RNA amplification device referred to hereinafter as "the paper-based RNA amplification device 2." A paper pad 2a of the device 2 is laminated between two layers of thermoplastic films 2b and 2c of the device 2 in the manner in which a common identification card is fabricated. FIG. 1B shows the paper-based RNA amplification device 2 attached to a polycarbonate container 3 via an adhesive tape 4. FIG. 1C shows a cross-sectional side view of the mechanism of the bearing ball valve 5 of the SPRA rotatable reservoir unit 6. The valve 5 is actuated by a pillar 7 of the SPRA collector 8 pushing the bearing ball 9 up to discharge the liquid housed in the reservoir. FIG. 1D shows the SPRA apparatus 1, which includes the SPRA collector 8 and a buffer unit 6.

In accordance with this representative embodiment, the buffer unit 6 is a rotatable buffer unit referred to hereinafter as "the SPRA rotatable reservoir unit 6." The SPRA rotatable reservoir unit 6 and the SPRA collector unit 8 are assembled together via a pin 11. Thus, the SPRA rotatable reservoir unit 6 is rotatably coupled to the SPRA collector 8. The rotatable SPRA reservoir unit 6 includes three reservoirs to separately house the binding buffer and the two wash buffers. The SPRA collector 8 functions as a sample collector with the laminated paper-based RNA amplification device 2 attached underneath. FIG. 1E shows a lure-lock-threaded lid 13 of the SPRA rotatable reservoir unit 6 with an O-ring used to prevent liquid leakage during transportation. A protruded peg underneath the lid 13 is designed to press down the bearing ball once the lid 13 is tightened, as will be described below in more detail.

Three of the lids 13 of different sizes are used to seal the binding buffer 6a and the two wash buffers 6b and 6c of the SPRA rotatable reservoir unit 6 to prevent spillage during transportation. The design can be the same for all of the lids, but lids of the wash buffers 6b and 6c are smaller in diameter than the lid of the binding buffer 6a. Securing the lids to the respective buffers 6a-6c causes the ball bearing valves of the buffers 6a-6c to be locked in the closed positions.

FIGS. 2A-2F are top perspective views of the SPRA apparatus 1 and the VIVAS 12 at various stages during use. The SPRA collector 8 is mechanically coupled to the bottom of the VIVAS 12 by a 3D-printed device holder 14. The detection scheme for viruses collected from aerosols is as follows. The virus particles in the aerosol are enlarged by the VIVAS 12 and impinged directly into the lysis buffer housed in the reservoir of the SPRA collector 8, as shown in FIG. 2A. After a 15-minute collection period, the SPRA collector 8 was removed from the VIVAS 12 and assembled with the rotatable SPRA reservoir unit 6, as shown in FIG. 2B. The rotatable SPRA reservoir unit 6 was then rotated to discharge the binding buffer 6a into the virus lysate held in the SPRA collector 8. The laminated paper-based RNA amplification device 2 underneath the SPRA collector 8 filtered the virus RNA from the lysate. Once the lysate filtration process was completed, the rotatable SPRA reservoir unit 6 was rotated to discharge the two wash buffers 6b and 6c sequentially, as indicated by FIGS. 2C and 2D. The whole RNA purification process took around 25 minutes, depending on the collected volume. The laminated paper-based RNA amplification device 2 was then peeled from the collector 8 and taped onto the polycarbonate container 3 for RT-LAMP amplification. After a 25-minute incubation period, as depicted in FIG. 2E, the amplified DNA could be detected using 1 µL SYBR Green dye and a blue LED flashlight, as shown in FIG. 2F.

FIG. 3A shows a top-view photograph of the rotatable SPRA reservoir unit 6 shown in FIGS. 1D and 1E. FIG. 3B shows top-view and bottom-view photographs of the rotatable SPRA reservoir unit 6 with the lids 13 attached to the respective buffers 6a-6c. FIG. 3C shows a side-view photograph of the VIVAS 12 having the device holder 14 (FIG. 2A) mechanically coupled to the bottom of the VIVAS 12. As indicated above with reference to FIG. 2A, the device holder 14 couples the SPRA collector 8 to the VIVAS 12. FIG. 3D shows a top-view photograph of the device holder 14 holding the SPRA collector 8. FIG. 3E shows a bottom-view photograph of the device holder 14.

Experimental Description

Virus and its Preparation

The following is a discussion of an experiment that was conducted using the integrated SPRA-VIVAS platform described above with reference to FIGS. 1A through 3E. MDCK (CCL-34; Madin-Darby Canine Kidney Epithelial Cells) were obtained from the American Type Culture Collection (Manassas, VA, USA) and were propagated as monolayers at 37° C. and 5% $CO_2$ in Advanced Dulbecco's Modified Eagle's Medium (aDMEM) (Invitrogen, Carlsbad, CA, USA) supplemented with 2 mM L-Alanyl-L-Glutamine (GlutaMAX, Invitrogen), antibiotics (PSN; 50 µg/mL penicillin, 50 µg/mL streptomycin, 100 µg/mL neomycin (Invitrogen)), and 10% (v/v) low IgG, heat-inactivated gamma-irradiated fetal bovine serum (HyClone, Logan, Utah).

Prior to use, all cell lines were treated for 3 weeks with plasmocin and verified free of *mycoplasma* DNA by PCR. T75 flasks of newly confluent MDCK cells were infected with 100 µL of Influenza Virus A/Mexico/4108/2009

(pH1N1), a wild-type H1N1 pandemic 2009 strain, in 5 mL of serum-free aDMEM supplemented as previously described plus L-1-tosylamido-2-phenylethyl chloromethyl ketone (TPCK)-treated *mycoplasma*-free and extraneous virus-free trypsin (Worthington Biochemical Company, Lakewood, NJ) and incubated in 5% $CO_2$ at 33° C. The TPCK trypsin was used at a final concentration of 2 μg/mL for MDCK. After 4 hours of incubation, 3 mL of serum-free aDMEM supplemented with TPCK trypsin was added. After CPE were observed in over 50% of cells, the cells were scraped, and the virus was collected and frozen at −80° C. A virus stock solution of $6.4\times10^6$ $TCID_{50}$/mL was used for sample spiking and RNA extraction.

RT-LAMP Amplification

RNA was extracted from 140 μL of H1N1 flu virus samples using a QIAamp Viral RNA Mini Kit (QIAGEN, Valencia, CA, USA) following manufacturer's protocol. The collected RNA was eluted with 60 μL of buffer AVE (QIAGEN) and stored at −80° C. before use. RNA extracted from H1N1 flu virus was used to conduct reverse transcriptase loop-mediated isothermal amplification (RT-LAMP). Each 25 μL RT-LAMP system contains 2.5 μL of 10× isothermal amplification buffer, 1.4 mM dNTPs, 6 mM $MgSO_4$, 2.5 μL of 10× primer mix, 8 U Bst 2.0 WarmStart® DNA Polymerase, 7.5 U WarmStart® RTx Reverse Transcriptase, and 1 μL RNA sample. Except for the dNTPs from ThermoFisher Scientific (MA, USA), other reagents in the RT-LAMP system was obtained from New England Biolabs (Ipswich, MA, USA). The primer mix contains 1.6 μM F1P/B1P, 0.2 μM F3/B3, and 0.4 μM LF/LB. The sequences of possible primers are listed below in Table 1. The inventors followed the primer designs in the literature; they used the first set of primers though other sets of primers can be used as will be understood by those of skill in the art in view of the description provided herein. These primers were obtained from Integrated DNA Technologies (Coralville, Iowa, USA). To perform the amplification, the RT-LAMP system was incubated at 63° C. for 30 minutes in a Bio-Rad Mycycler® (Bio-Raid, CA, USA). The amplicons were confirmed with 2% agarose gel electrophoresis. Gel bands were imaged using a Gel Doc™ EZ system (Bio-Rad).

Table 1. Possible sequences of RT-LAMP primers for H1N1 flu virus detection Primer Sequence (5'-3') Ref.

TABLE 1

Possible sequences of RT-LAMP primers for H1N1 flu virus detection

| Primer | Sequence (5'-3') | Ref. |
|---|---|---|
| F3 | ACCTTCTAGAAGACAAGCATAA | 1 |
| B3 | TCCTCATAATCGAT | |
| FIP | TGGATTTCCCAGGATCCAGCGGAAACTATGCAAACTAAGAGG | |
| BIP | TCCACAGCAAGCTCATGGTCTCCTGGGTAACACGTTCC | |
| LF | CCAAATGCAATGGGGCTAC | |
| LB | CTACATTGTGGAAACATCTAGTTCAG | |
| F3 | AGACGCTTTGTCCAAAATGC | 2 |
| B3 | TCACAAGTGGCACACACTAG | |
| FIP | CCTTGGCCCCATGGAACGTTATGGGGACCCGAACAACATG | |
| BIP | TTCAACTGGTGCACTTGCCAGTGTGGTCACTGTTCCCATCC | |
| LF | TGAGCTTCTTGTATAGTTTAACTGC | |
| LB | TGCATGGGCCTCATATACAACA | |
| F3 | AAGCTCAGCAAATCCTACA | 3 |
| B3 | TCCCTCACTTTGGGTCTT | |
| FIP | GACTTTGTTGGTCAGCACTAGTAGAAAAGGGAAAGAAGTCCTCG | |
| BIP | TCTATCAGAATGCAGATGCATATGTTGCTATTTCCGGCTTGAA | |
| LF | GATGGTGAATGCCCCATAGC | |
| LB | TTTTGTGGGGTCATCAAGATACAG | |
| F3 | AAGCTCAGCAAATCCTACA | 4 |
| B3 | TCCCTCACTTTGGGTCTT | |
| FIP | GACTTTGTTGGTCAGCACTAGTAGATTTTAAAGGGAAAGAAGTCCTCG | |
| BIP | TCTATCAGAATGCAGATGCATATGTTTTTTGCTATTTCCGGCTTGAA | |
| LF | GATGGTGAATGCCCCATAGC | |
| LB | TTGTGGGGTCATCAAGATACAGC | |
| F3 | CAGACTAGGCAGATGGTAC | 5 |
| B3 | TCAGGTGCAAGATCCCAATG | |
| FIP | GCCTGCAAATTTTCAAGAAGGTCTTTTGCAATGAGAACTATTGGGACTC | |
| BIP | CCAGAAGCGAATGGGAGTGCTTTTATTTGCTGCAATGACGAGAG | |
| LF | AGACCAGCACTGGAGCTAGG | |
| LB | GATGCAGCGATTCAAGTGATC | |
| F3 | CCGGGAGACAAAATAACATTC | 6 |
| B3 | GTATATTCTGAAATGGGAGGC | |
| FIP | CAGATCCAGCATTTCTTTCCATTGGAAGCAACTGGAAATCTAGTG | |
| BIP | TATCATTTCAGATACACCAGTCCACTGGTGTTTATAGCACCCTTG | |
| LF | CGAATGCATATCTCGGTAC | |
| LB | ATACAACTTGTCAAACACC | |

Note:
FIP stands for Forward Inner Primer;
BIP stands for Backward Inner Primer;
LF and LB are the forward and backward loop primers.

To verify the incubation time required for the H1N1 flu virus RT-LAMP primers, a real-time RT-LAMP assay was carried out. To enable real-time amplicon detection, 0.5 μL of 10× concentrate SYBR green I nucleic acid gel stain in DMSO (ThermoFisher Scientific) and 0.5 μL ROX reference dye (ThermoFisher Scientific) were added to the 25 μL RT-LAMP reaction buffer. The fluorescence signal was read through the QuantStudio 3 real-time PCR system (ThermoFisher Scientific).

Note: FIP stands for Forward Inner Primer; BIP stands for Backward Inner Primer; LF and LB are the forward and backward loop primers.

Paper-Based RNA Isolation

The laminated paper-based RNA amplification device 2 (FIGS. 1A and 1B) contains a polycarbonate container, a double-sided adhesive tape, and a laminated paper pad. Three kinds of paper materials, the FTA© classic card (ThermoFisher Scientific), the Whatman™ 1 Chr chromatography paper (ThermoFisher Scientific), and the Whatman™ GF/F glass microfiber filter (ThermoFisher Scientific) were studied for fabricating the paper-based RNA isolation device. A 3.5-mm-diameter round pad of the paper material was made using a steel puncher. Two layers of thermoplastic films were shaped by cutting a section of 75 μm thick polyester thermal bonding lamination films (Lamination Plus, Kaysville, UT, USA) using a Graphtec Craft Robo-S cutting plotter (Graphtec Corporation, Yokohama, Japan). To laminate the device, the paper pad and the top and bottom films were aligned and passed through a heated laminator (GBC® Catena 65 Roll Laminator, GBC, Lake Zurich, IL, USA), which was set at a rolling speed of "1" with the temperature at 220° F. After lamination, the laminated paper pad was attached to a 3 mm thick, 2 cm×2 cm square polycarbonate container via a piece of 3M 9087 white bonding tape (R. S. Hughes, Sunnyvale, CA) to form the final device. The container was shaped from a piece of clear polycarbonate sheet (McMaster-Carr, Elmhurst, IL) using a milling machine (Sherline Products, Vista, California). A 3-mm-diameter round hole was made in both the polycarbonate container and the double-sided adhesive tape to align with the paper pad as a sample loading port.

The lysis product mixture of H1N1 flu virus was used to test the performance of laminated paper-based RNA amplification device. Aliquots containing 10, 1, and 0.1 $TCID_{50}$ H1N1 flu virus lysis per μL were made with the flu virus stock solution and molecular-biology-grade water and buffer AVL (QIAGEN) at the ratio of 1:4 and stored at −80° C. before use. To compare the RNA capture efficiency of laminated paper-based RNA amplification device made of FTA® card, chromatography paper and glass microfiber paper, a series dilution of 70 μL H1N1 flu virus lysis (made from virus spiked water and AVL lysis buffer in the ratio of 1:4) was used to compare the limit of detection (LOD) of each material. An ethanol (200 proof) solution of 56 μL was mixed into the diluted virus lysis before introducing to the device. A solution of 100 μL each AW1 (QIAGEN) and AW2 (QIAGEN) of 100 μL each was then filtered through the paper pad sequentially to purify the RNA captured by the device.

To detect the RNA captured, a piece of adhesive tape (Fellows®) 4 (FIG. 1B) was attached to the bottom of the device 2 (FIGS. 1A and 1), and 25 μL RT-LAMP amplification buffer was loaded to the paper pad. The device 2 was then sealed with another piece of adhesive tape on the top. The sealed device was incubated at 63° C. for 25 minutes in an Isotemp 105 water bath (ThermoFisher Scientific) for DNA amplification. The amplicons were analyzed with gel electrophoresis as described above.

Virus Detection Using the SPRA

As indicated above, in accordance with an embodiment, 3D-printed sample preparation components were designed to incorporate the laminated paper-based RNA amplification device 2 to form the final SPRA apparatus 6. These components could be used to perform viral RNA purification without using lab tools such as a pipette, for example. The sample preparation components were fabricated with a commercial 3D printer, Ultimaker 3 (Ultimaker, Geldermalsen, Netherlands), using polylactic acid (PLA) filament with polyvinyl alcohol (PVA) as support material. It should be noted, however, that the inventive principles and concepts are not limited to these components being formed via 3D printing, as will be understood by those of skill in the art in view of the description provided herein. Alternatives to 3D printing for making these parts include molding, milling, machining, and other manufacturing and fabrication methods.

The print layer height was set to 0.06 mm and the infill density was set to 100%. As shown in FIG. 1D, the 3D-printed sample preparation components contain two units. The SPRA rotatable reservoir unit 6 comprises the buffer reservoir 6a housing the binding buffer (molecular-biology grade ethanol) and the two wash buffers (AW1 & AW2, QIAGEN) 6b and 6c for RNA purification. The bottom unit of the SPRA apparatus 1 is the aforementioned SPRA collector 8 where the laminated paper-based RNA amplification device 2 was attached with a piece of double-sided tape. The SPRA apparatus 1 was assembled by inserting the pin 11 through one hole located in each unit. A photo of the SPRA apparatus 1 compared to a U.S. quarter is shown in FIG. 3A.

A simple fluid control valve, the "bearing ball" valve shown in FIG. 1C, was employed to trigger the release of buffers from the buffer reservoirs 6a-6c to the SPRA collector 8 of the SPRA apparatus 1. The valve was inspired by the small animal water bottle in which water flowed out when a drinking animal pressed against the bearing ball blocking the water dispensing tube. As shown in FIG. 1C, a 5/16-inch-diameter opening was designed at the bottom of the funnel-shaped reservoirs 6a-6c to house a stainless-steel bearing ball 9. The opening was designed in such a way that the bearing ball could block the opening while protruding 2 mm from the bottom of the buffer reservoir. The bearing ball 9 functioned as a plug to keep the liquid from flowing out. The bearing ball valve could be triggered by rotating the reservoir unit until the ball was pushed up by a pillar 7 (FIG. 1D) in the center of the collector 8. To prevent possible reagent contamination during transportation, the lid 13 (FIGS. 1E and 3B) with a lure-lock thread and a piece of O-ring (McMaster-Carr) was used. The lid 13 contained a peg underneath that pressed against the bearing ball 9 while the thread was tightened. The lid 13 achieved a leak-free seal when the device was rotated upside down.

Virus Aerosol Generation and Sampling

The aforementioned H1N1 flu virus was used for virus aerosol generation and testing. All the sampling experiments were performed in a US Department of Agriculture inspected-and-approved BSL2-enhanced laboratory following BSL3 work practices. To generate flu virus aerosols, 10 mL of 1×10⁵ $TCID_{50}$/mL H1N1 flu virus solution in phosphate-buffered saline (PBS) plus 0.5% (w/v) bovine serum albumin (BSA) fraction V was used with a 6-jet BioAerosol Nebulizing Generator (BANG, CH Technologies).[25-27] HEPA-filtered room air was used to provide air flow for the BANG.

The VIVAS 12 (FIGS. 2A and 3C), a laminar-flow, water-based condensational growth system, was used to amplify the virus aerosols generated by the BANG and has been described previously. To integrate the SPRA apparatus 1 with the VIVAS 12, the device holder 14 was designed to fixate, or mechanically couple, the SPRA collector 8 to the VIVAS' aerosol outlet with four screws. A rubber pad was used to form an air-tight seal to prevent aerosol leakage during sampling (FIG. 3C). Fluorescein aerosols were used to demonstrate the collection result. As shown in FIG. 3E, the collected droplets deposited by the 32 nozzles of the VIVAS could be observed in the SPRA collector 8.

As described previously, the conditioner (the top half) of the VIVAS 12 was cooled to 6° C., and the initiator (the bottom half) was heated to 45° C. An air flow rate at six liters per minute (LPM) was introduced into the VIVAS 12. A negative control sample was first collected with 10 mL PBS plus 0.5% (w/v) BSA in the BANG for 15 minutes. Three positive collections with virus solution in the BANG were performed for 15 minutes each. A lysis buffer (buffer AVL) of 560 μL was preloaded to the SPRA collector 8 where the aerosols from the VIVAS 12 directly impinged. The lysis buffer protected viral RNA from RNase degradation and deactivated the collected virus to reduce the generation of biohazardous wastes. Between each collection, a washing step consisting of 5-minute collection of 0.01% sodium dodecyl sulfate (SDS, ThermoFisher Scientific) solution in the BANG and then 25-minute collection of molecular-biology grade water in BANG was performed to flush the virus aerosols in the system from a previous sampling.

Detection of Collected Virus Aerosols

After the 15-min sampling period, the SPRA collector was removed from the VIVAS 12 by loosening screws and assembled with the top reservoir unit 6 (FIG. 1D). The assembled SPRA apparatus 1 was first placed on top of a piece of blotting paper to provide capillary forces for the RNA purification process. The binding buffer 6a (560 μL ethanol) was discharged right after to enhance RNA binding to the laminated paper pad. The blotting process took roughly 15 minutes, depending on the volume of sample collected and the type of absorbent used. After all the lysate was filtered through the laminated paper pad, the reservoir unit 6 of the SPRA apparatus 1 was rotated to add the first wash buffer 6b (250 μL AW1) to the collector 8, and the top reservoir unit 6 was rotated again, and the second wash buffer 6c (250 μL AW2) was discharged and filtered through in the same manner. The two wash steps took roughly 5 minutes to complete.

To detect the purified RNA from the virus aerosols, the laminated paper-based RNA amplification device 2 was peeled from the SPRA collector 8 and taped to its polycarbonate container 3 (FIG. 1B) to conduct RT-LAMP amplification as described previously. After 25 minutes incubation, 1 μL of 10,000× concentrate SYBR green I nucleic acid gel stain was added to the amplicons, and the results can be read by a naked-eye. Alternatively, an ULAKO blue LED flashlight (Amazon, WA, USA) (FIG. 2F) powered by an AA battery was used to excite the green fluorescence from the amplicon-SYBR complexes. The resulting color of the solution was imaged using a smart phone. A piece of brown-tainted translucent plastic film was taped in front of the phone camera lens to filter out the excess blue light from the LED flashlight. It should be noted that other light sources such as lamps and various diodes, for example, can be used for this purpose, as will be understood by those of skill in the art in view of the description provided herein.

Results and Discussion

Real-Time RT-LAMP Detection

FIG. 4A is a graph showing curves 16, 17, 18 and 19 representing normalized fluorescent signals of 10, 100, 1000 and no-temperature control (NTC), respectively, $TCID_{50}$ H1N1 flu virus genome equivalents as a function of RT-LAMP time. The curves 16-19 indicate that all samples' amplification signals reached the plateau in 20 minutes. FIG. 4B is a plot of a standard curve (log $TCID_{50}$ per reaction vs. threshold time) generated with three replicates of each serial diluted H1N1 flu virus RNA samples. The QIAamp Viral RNA Mini Kit (QIAGEN) was used as a bench top standard to purify RNA from aqueous samples spiked with H1N1 flu virus. Fluorescence readings were taken from RT-LAMP containing 10, 100 an(a) d 1000 $TCID_{50}$ RNA equivalents using the QuantStudio 3 real-time PCR system (FIG. 4A). All the wells containing flu virus RNA were observed with a signal within 20 minutes, and no non-specific amplification was observed during the 30-minute incubation period. This result suggested that a 25-minute incubation was sufficient to detect the flu virus RNA isolated by our device. The linear-shaped standard curve (FIG. 4B) indicated that quantitative virus aerosol detection can be achieved by the integrated SPRA-VIVAS platform with portable optical sensors.

Paper-Based RNA Isolation

The laminated paper-based RNA amplification device 2 used in the experiment was made as follows. A lamination technique was used to prepare a piece of paper pad so that it could be used as a filter for RNA in the same manner of the commercially available nucleic acid purification spin column. The chaotropic-salt-based buffers from QIAamp Viral RNA Mini Kit (QIAGEN) was used to improve RNA binding to the paper substrate. The polycarbonate container 3 (FIG. 1B) was attached to the laminated paper pad as a sample well to form the paper-based RNA amplification device. Instead of centrifugation force, sample filtration was powered by capillary forces generated in porous paper and the absorbent pad beneath the paper-based RNA amplification device. H1N1 flu virus was used to demonstrate RNA purification and amplification in the device 2. The amplicons were analyzed using agarose gel electrophoresis and ethidium bromide staining.

To select an effective binding material for RNA, devices were fabricated using FTA® card, the Whatman™ Chr chromatography paper, and the Whatman™ GF/F glass microfiber filter for comparison. The FTA® card is a commercialized filter paper specifically treated to extract, bind, and preserve nucleic acids from blood, plant and animal tissue extracts and other sources according to the manufacturer. The chromatography paper is an untreated, high quality cellulose fiber paper. The GF/F glass microfiber filter is a paper specifically designed for nucleic acid purification. Paper-based devices made of FTA® card, glass microfiber and chromatography paper were tested with different concentrations of H1N1 virus lysis to compare the limit of detection (LOD). The results indicated that the device made of chromatography paper had the lowest LOD, detected spiked samples of 0.8 $TCID_{50}$ flu virus, while the device made of FTA® card and glass microfiber detected 5 $TCID_{50}$.

Untreated cellulose has been used as a nucleic acid isolation material since the 1960s, though its use is far less common than silica. This is possibly due to the complicated steps of assembling cellulose powder into a column often involved. Those manual steps make the cellulose powder less desirable compared to the ready-to-use silica column. The laminated paper-based RNA amplification device 2, on the other hand, is easy to make, of low cost, and does not require complicated manual steps during usage. The result discussed above suggests that the cellulose chromatography paper has a great potential as a RNA extraction substrate. As a result, all of the following experiments were performed using devices made from chromatography paper. It should be noted, however, that the inventive principles and concepts are not limited to using any particular type of extraction/amplification device for this purpose.

Detection of Flu Virus in Water

A H1N1 flu virus spiked water of 140 μL was lysed with 560 μL buffer AVL and tested with the SPRA apparatus 1 to evaluate its performance in handling samples with the same volume range of those collected by the VIVAS 12 at 6 LPM for 15 minutes. The volume ratio of sample-lysis-ethanol was kept at 1:4:4 as instructed by the QIAamp Viral RNA mini Kit's manufacturer.

The RNA purification and amplification process each took roughly 25 minutes to complete, after which the result could be read using SYBR green dye and blue LED flashlight without lab instruments. As shown in FIGS. 5A-5C, 1 $TCID_{50}$ H1N1 flu virus per 140 μL sample was successfully detected in one hour using the SPRA apparatus 1. The SYBR green-DNA-complex absorbs blue light and emits green light, resulting in a light-yellow color (FIG. 5A) when observed under the ambient light and a bright green fluorescence under blue LED (FIG. 5B). SYBR green was chosen for the experiment as it detects the DNA amplicons directly, while other colorimetric RT-LAMP methods such as the hydroxynaphthol blue, the leuco crystal violet, and the phenol red[39] detect the by-products of DNA amplification.

Detection of H1N1 Flu Virus Aerosols

The average collection volume of the integrated SPRA-VIVAS system for a 15-minute sampling using 10 mL PBS/BSA media in the BANG and 6 LPM air flow rate for the VIVAS was determined by weighing the SPRA collector 8 before and after collection to be 143±25 µL (mean±standard deviation). As a result, 560 µL lysis buffer was used in the SPRA collector 8 for the H1N1 flu virus aerosol detecting experiment. A virus concentration of $1\times10^5$ $TCID_{50}$/mL H1N1 flu virus in PBS/BSA was used in the BANG and sampled in triplicates. According to the infectious H1N1 virus collection efficiency reported by the inventors in literature, the amount of collected H1N1 flu virus is above the sensitivity of the SPRA apparatus 1.

Figures 6A, 6B, 6C:
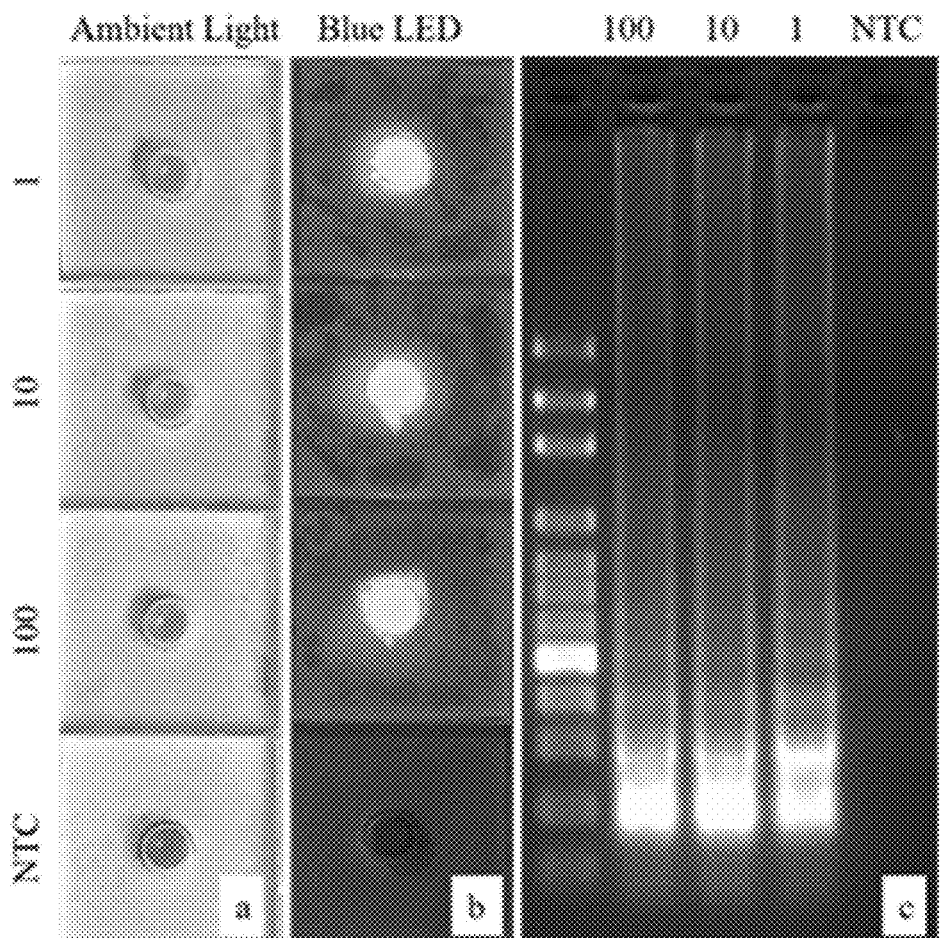
FIGS. 6A-6C are photographs showing how the apparatus shown in FIGS. 1A-1E was used to successfully detect the H1N1 flu virus aerosols generated in a lab.

The SPRA apparatus 1 successfully detected the H1N1 flu virus aerosols generated in lab (FIGS. 6A-6C). No nonspecific amplification was observed in the negative control collection of PBS/BSA aerosols. Strong fluorescence signals were observed from all the triplicates of the H1N1 flu virus aerosol collections. Including the sampling time, one virus aerosol detection process only took around 65 minutes to complete, proving the SPRA apparatus 1 to be fast and effective in assessing airborne influenza virus transmission risks and/or in screening the presence of a certain type of airborne virus in the environment.

SPRA-VIVAS Platform Conclusions

The integrated SPRA-VIVAS platform detected lab-generated H1N1 flu virus aerosols in one hour. This system features a two-step concentration for the sporadic virus aerosols: (a) the concentration of liters of virus aerosols into a 150 µL aqueous sample, and (b) the filtration of lysed virus aerosol RNA onto the laminated paper pad. The two-step concentration provides the platform with the sensitivity required to detect virus aerosols using a rapid, specific RT-LAMP method. Moreover, the laminated paper-based RNA amplification device 2 used as a filter was able to process a flexible amount of collected aerosol sample, thus allowing the sensitivity to be increased by increasing the collection time, i.e., the volume of aerosol collected by the VIVAS 12, if necessary.

The detection limit of the SPRA-VIVAS platform can be explored using virus aerosols of different concentrations and a portable optical sensor for quantitative detection. The collection of real-world virus aerosols can also be performed in places such as infirmaries and classrooms. On the other hand, the superior sensitivity and high portability of the SPRA apparatus 1 in RNA virus detection over the commercial FTA® card and Whatman™ glass microfiber has been demonstrated herein. Except for detecting collected virus aerosols, the SPRA apparatus 2 can also be used to detect virus from other types of aqueous samples.

Having described the SPRA apparatus and method for performing airborne virus detection in accordance with a representative embodiment, the apparatus and method for detecting non-airborne viruses will now be described with reference to a representative embodiment and an example application in which the virus being detected is the Zika virus.

In the following description, a valve-enabled lysis, paper-based RNA enrichment, and RNA amplification device (VLEAD) apparatus and method for sample-to-answer Zika virus detection are presented. It should be noted, however, that the VLEAD apparatus and method are suitable for providing sample-to-answer virus detection for viruses other than the Zika virus. In accordance with a representative embodiment, the VLEAD apparatus comprises 3D-printed components for sample preparation and a laminated paper pad for RNA enrichment. The valving mechanism described above with reference to FIG. 1C is incorporated into the VLEAD apparatus design to enable RNA extraction to be conducted without the help of even basic lab equipment such as a pipette. Instead of choosing popular paper materials such as the FTA® card, in accordance with a representative embodiment, untreated, cellulose chromatography paper is used as an RNA binding material to reduce the fabrication cost and potential inhibitory effect on RT-LAMP amplification.

In accordance with a representative embodiment, RT-LAMP amplification is performed using a commercially available, controllable, battery powered "smart" coffee mug (Ember™ Travel Mug) as a water bath to heat the device. A variety of portable electrical and chemical heaters have been developed for POC diagnostic devices using isothermal DNA amplification, but they are often not readily available to average users and thus require further fabrication and calibration. On the other hand, the Ember™ coffee mug is carried by many Starbucks® coffee shops in the U.S. and major online vendors such as Amazon and eBay, and its temperature can be accurately controlled using a smartphone software application program (App). For naked-eye result reading, in accordance with a representative embodiment, a SYBR green dye and a relatively inexpensive blue LED flashlight are used to get an explicit fluorescence signal from the positive test.

The duration Zika virus can be detected in blood, saliva, urine and semen ranges from days to months after symptom onset. To demonstrate some of the inventive principles and concepts, the inventors have chosen urine and saliva to demonstrate that the sample collection processes performed using the VLEAD apparatus and method are simple and non-invasive. The inventors also used Zika virus spiked water to compare the sensitivity of the VLEAD apparatus with a commercial QIAamp Viral RNA mini Kit (QIAGEN). After validating the VLEAD apparatus and method using Zika virus spiked samples, the inventors successfully detected Zika virus in a clinical urine sample collected in 2016.

VLEAD Design and Fabrication

FIGS. 7A-7D are perspective views of components comprising the VLEAD apparatus 20 in accordance with a representative embodiment. As shown in FIGS. 7A-7D, the VLEAD apparatus 20 comprises three parts, namely, a buffer unit 21 (FIG. 7A), a collector or mixing unit 22 (FIG. 7B) (referred to hereinafter as "the mixing unit 22"), and a detection unit 23 (FIG. 7C), which may be identical to paper-based RNA amplification device 2 shown in FIG. 1A. The mixing unit 22 is integrated with the detection unit 23 by inserting the bottom protrusion 28 (FIG. 7B) of the mixing unit 22 into the center hole 26 in the detection unit 23 with a piece of double-sided adhesive tape disposed between the two units being used to fix them together.

In accordance with this representative embodiment, the buffer unit 21 is slidably coupled with the mixing unit 22 via a sliding mechanism 27. In accordance with a representative embodiment, the sliding mechanism 27 comprises a pair of rails 27a on the mixing unit 22 that engages a pair of grooves 27b on the buffer unit 21.

A commercial 3D printer, the Ultimaker 3 (Ultimaker, Geldermalsen, Netherlands) was used to fabricate the buffer unit 21 and the mixing unit 22. The devices were printed from polylactic acid (PLA) with polyvinyl alcohol (PVA) as support material. The print layer height was set to 0.06 mm and the infill density was set to 100%. Both the buffer unit 21 and the mixing unit 22 can also be made by injection molding, machining, and other methods, as will be understood by those of skill in the art in view of the description provided herein.

The detection unit 23 contained a polycarbonate container, a double-sided adhesive tape, and a laminated paper pad. To fabricate the laminated paper pad, a 3.5-mm-diameter circle of the Whatman™ 1 chromatography paper (Fisher Scientific, Pittsburgh, PA, USA) was made using a steel puncher. Two layers of thermoplastic films were shaped by cutting a section of 75 μm thick polyester thermal bonding lamination films (Lamination Plus, Kaysville, UT, USA) using a Graphtec Craft Robo-S cutting plotter (Graphtec Corporation, Yokohama, Japan). The paper pad and the cover and bottom films were then aligned and passed through a heated laminator (GBC® Catena 65 Roll Laminator, GBC, Lake Zurich, IL, USA), which was set at a rolling speed of "1" with the temperature at 220° F.

After lamination, the laminated paper pad was attached to a 3 mm thick, 2 cm-by-2 cm square polycarbonate container via a piece of 3M 9087 white bonding tape (R. S. Hughes, Sunnyvale, CA) to form the RNA detection unit. The container was shaped from a piece of clear polycarbonate sheet (McMaster-Carr, Elmhurst, IL) using a milling machine (Sherline Products, Vista, California). A photo of the device is shown in FIGS. 8(a) and (b) with a quarter as a comparison in size.

Fluid control valves 31 (FIG. 7D), that are identical to the fluid control valve shown in FIG. 1D in accordance with this representative embodiment, are disposed in the buffer unit 21 for triggering the release of buffers from the buffer unit 21 into the reservoir 22a of the mixing unit 22. As shown in FIG. 7D, a 4-mm-diameter opening 29 was designed at the bottom of the funnel-shaped reservoirs 21a-21d of the buffer unit 21 to house a stainless-steel bearing ball 24. This opening 29 was designed in a way that the bearing ball 24 blocks the opening while protruding 1.5 mm from the bottom of the buffer reservoirs 21a-21d. Two rectangular gaps 22b are formed in a wall 22c of the mixing unit 22 so that the bearing ball can pass through while the buffer unit 21 slides along the mixing unit 22. The bearing ball 29 functions as a plug to keep the buffer from flowing out of the reservoirs 21a-21d until the bearing ball 29 is pushed up by the post 25 of the mixing unit 22 when the mixing unit 22 is sliding along the buffer unit 21.

Figures 8A, 8B, 8C:
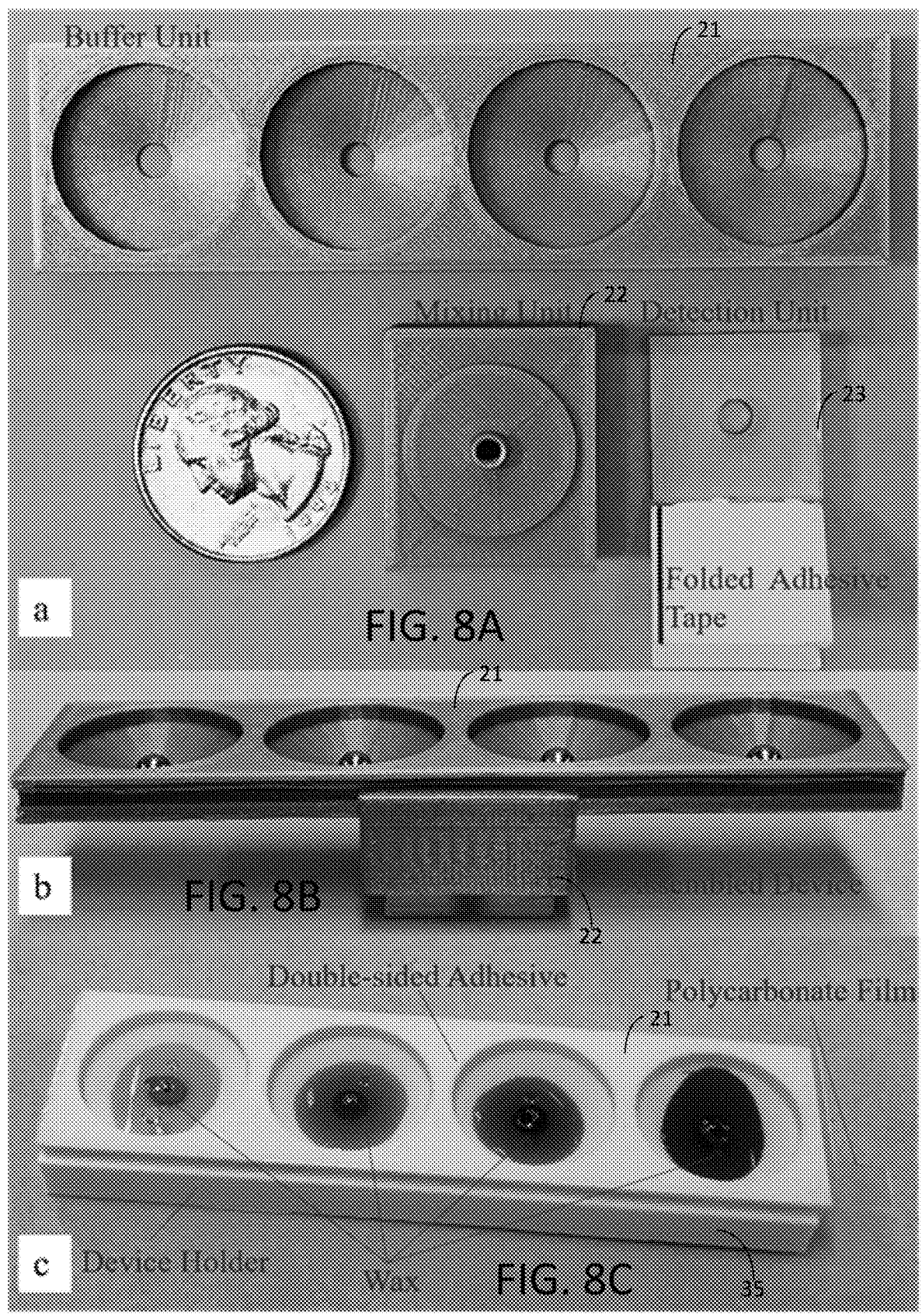
FIGS. 8A-8C are photographs of the apparatus shown in FIGS. 7A-7D.

FIGS. 8A-8C are photographs of the apparatus shown in FIGS. 7A-7D and its components. To prevent accidental triggering of the fluid control valves 31 during device transportation and storage, a sealing system was employed using wax and cover film to seal the buffer unit 21 (FIG. 8C). A small amount of Akrowax™ 130 (Akrochem, Akron, OH, USA) was placed at the bearing ball 24 to melt and re-solidify, so that it could form a breakable bond between the bearing ball 24 and the buffer unit 21. The bottom of the buffer unit 21 was further protected by sliding it into a device holder 35 (FIG. 8C). After loading the required buffers, a piece of polycarbonate film was taped to the top of the buffer unit 21 via double-sided adhesive to prevent buffer evaporation and spillage, and then the buffer unit 21 coupled to the device holder 35 (FIG. 8C) was ready for shipping and/or long-term storage.

Materials and Methods

Virus and its Preparation

Vero E6 (CRL-1586; African green monkey kidney epithelial cells) were obtained from American Type Culture Collection (ATCC, Manassas, VA, USA) and cultured in Advanced Dulbecco's Modified Eagle's medium (aDMEM) with 10% low antibody, gamma-irradiated, heat inactivated fetal bovine serum (FBS), GlutaMAX, and Penicillin-Streptomycin-Neomycin (PSN) at 37° C. with 5% $CO_2$.

A Zika virus (ZIKV) strain from Puerto Rico (PRV-ABC59) was obtained from Biodefense and Emerging Infections Research Resources Repository (BEI Resources, Manassas, VA, USA). The strain was grown up for a lab stock by inoculating 475 μL media (aDMEM with 3% FBS, GlutaMAX, and PSN) with a ratio of 25 μL virus to a monolayer of Vero E6, and gently rocking once every 15 minutes at 37° C. with 5% $CO_2$ for 1 hour. A T25 (25 cm² growth surface) flask with Vero E6 cells at 60% confluency was used for observation of ZIKV-induced cytopathic effects (CPE). After allowing for virus adsorption for two hours, an additional 2 mL of aDMEM was added to the flasks, followed by incubation at 37° C. with 5% $CO_2$. Cultures were maintained with the replacement of 1 mL of aDMEM every 3 days for up to 10 days' post-inoculation, or until visual observation of ZIKV-induced CPE. Expected ZIKV-induced CPE were perinuclear vacuolation followed by apoptosis. Spent media (2 mL) was collected at initial observation of CPE, cells were refed with 2 mL of aDMEM, and final collections of spent media and lysed cells was taken when CPE were observed in 50% of the monolayer.

Plaque assays were performed to quantitate PRVABC59 and obtain viral titers, with newly confluent Vero E6 cells in a 6-well plate, to which 250 μL of virus dilutions of $10^2$, $10^3$, $10^4$, $10^5$, and $10^6$ in aDMEM were added to each well. After inoculation, the 6-well plates were rocked every 15 minutes for two hours at 37° C. with 5% $CO_2$. Inocula were then removed, the monolayer washed twice with serum-free Eagle's minimum essential medium (EMEM) and the cells overlaid with 3 mL of 1:1 solution of 1.6% melted agarose with EMEM and 3% low antibody, heat-inactivated, gamma-irradiated FBS with PSN. After the agarose solidified, the plates were incubated upside down for 5 days at 37° C. with 5% $CO_2$, after which an additional 2 mL overlay with 1:1 solution of 1.6% agarose and serum-free EMEM with 0.14 mg/mL neutral red was added. The plaque morphology was then observed, and the number of plaques were counted at 7 days post-infection. A virus stock solution of $1.5 \times 10^7$ plaque-forming unit (PFU)/mL was used for sample spiking and RNA extraction.

RT-LAMP Amplification

RNA was extracted from 140 μL of Zika virus samples using a QIAamp Viral RNA Mini Kit (QIAGEN, Valencia, CA, USA) by following the manufacturer's protocol. The collected RNA was eluted with 60 μL of buffer AVE (QIAGEN) and stored at −80° C. before use.

RNA extracted from Zika virus was used to conduct RT-LAMP. Each of 25 μL RT-LAMP system contains 2.5 μL of 10× isothermal amplification buffer, 2.5 μL of 10× primer mix, 8 U Bst 2.0 WarmStart® DNA Polymerase, 7.5 U WarmStart® RTx Reverse Transcriptase, a final concentration of 1.4 mM dNTPs and 6 mM $MgSO_4$, and 1 μL RNA sample. The 25-μL volume was brought up by molecular-biology-grade water. Except for the dNTPs from ThermoFisher Scientific (MA, USA), other reagents in the RT-LAMP system were obtained from New England Biolabs (Ipswich, MA, USA). The primer mix contains 1.6 μM F1P/B1P, 0.2 μM F3/B3, and 0.8 μM LF/LB, and the sequences of possible primers are listed below in Table 2. The primers were designed following the literature and obtained from Integrated DNA Technologies (Coralville, Iowa, USA). The inventors used the first set of primers in Table 2 though other sets of primers can be used, as will be understood by those of skill in the art in view of the description provided herein. To perform the amplification, the RT-LAMP system was incubated at 67° C. for 30 minutes in a Bio-Rad Mycycler® (Bio-Raid, CA, USA). The amplicons were confirmed with 2% agarose gel electrophoresis. Gel bands were imaged using a Gel Doc™ EZ system (Bio-Rad).

Table 2. Possible sequences of Zika RT-LAMP primers

TABLE 2

Possible sequences of Zika RT-LAMP primers

| Primer | Sequence (5'-3') | Ref. |
|---|---|---|
| F3 | TTGTCAGGCTCCTGTCAA | 7 |
| B3 | TTGCTACGAACCTTGTTGAT | |
| FIP | TGGCACCCTAGTGTCCACTTTTTAGGAATAGCCATGACCGA | |
| BIP | CAAGAAGGCACTCGTCAGGTTTTGTGTTTGCCTAGCTCTTT | |
| LF | TGCTGACCATACGGTGTG | |
| LB | GGTCTCTTCCTGGTTGTGG | |
| F3 | CAGTTCACACGGCCCTTG | 8 |
| B3 | TGTACCTCCACTGTGACTGT | |
| FIP | GGCGACATTTCAAGTGGCCAGAGAGCTCTAGAGGCTGAGA | |
| BIP | AGGGCGTGTCATACTCCTTGTGAGTGTTTCAGCCGGGATCT | |
| LF | CCTTCCCTTTGCACCATCCA | |
| LB | TACCGCAGCGTTCACATTCA | |
| F3 | TGGAGGGACAGGTACAAGT | 9 |
| B3 | TGTGGACCTCTCCACATGG | |
| FIP | CGCAGATACCATCTTCCCAGGCATCCTGACTCCCCCCGTA | |
| BIP | AAGGGGAGCTCAACGCAATCCGATCCCACAACGACCGTC | |
| LF | TGCTTGACTGCTGCTGCC | |
| F3 | TGACATCCCATTGCCTTGG | 10 |
| B3 | CTTCCCTTTGCACCATCCAT | |
| FIP | GGCGTGGGCATCCTTGAATTCTGCAGACACCGGAACTCCA | |
| BIP | GGCAAACCGTCGTCGTTCTGGCTCAGCCTCTAGAGCTCCA | |
| LF | TGCCTCTTTGTTGTTCCAGTG | |
| LB | AGCCGTTCACACGGCTC | |
| F3 | CGGATGGGATAGGCTCAAAC | 11 |
| B3 | ATGGACCTCCCGTCCTTG | |
| FIP | CCTGAGGGCATGTGCAAACCTAGAATGGCAGTCAGTGGAGAT | |
| BIP | ACCCTCAACTGGATGGGACAACTGGAGCTTGTTGAAGTGGTG | |
| LF | CATCAATTGGCTTCACAACGC | |
| LB | GGGAAGAAGTTCCGTTTTGCTC | |
| F3 | GACTTCTGCTGGGTCATG | 12 |
| B3 | GCCAACAATTCCGACACTA | |
| FIP | CCCCACTGAACCCCATCTATTGGGTCTTGGCGATTCTAGC | |
| BIP | GTTCAAGAAAGATCTGGCTGCCCCTCGTCTTCTTCTTCTCCT | |
| LF | GCTTGATTGCCGTGAATCTC | |
| LB | GCTGAGAATAATCAATGCCAGG | |

Note:
FIP stands for Forward Inner Primer;
BIP stands for Backward Inner Primer;
LF and LB are the forward and backward loop primers.

For real-time detection of the RT-LAMP assay, 0.5 μL of 1:1000 diluted 10,000× concentrate SYBR green I nucleic acid gel stain in DMSO and 0.5 μL ROX reference dye (ThermoFisher Scientific) were added to the 25 μL RT-LAMP reaction buffer. The fluorescence signal was read through the QuantStudio 3 real-time PCR system (ThermoFisher Scientific).

Zika Virus Detection Using the VLEAD

Zika samples were made by spiking 1 μL Zika virus at various concentrations to 140 μL of media. Water, human urine, and human saliva (Innovative Research, Novi, MI) were used to test the VLEAD's sensitivity. For safety concern, the Zika virus samples were mixed with the AVL lysis buffer (QIAGEN) at the ratio of 1:4 in a biosafety facility before bringing out to perform the test.

FIGS. 9A-9F depict the method for using the apparatus shown in FIGS. 7A-7D to perform testing. Two washing buffers (AW1 and AW2 buffer in QIAamp Viral RNA mini Kit) of 200 μL each, a binding buffer (200 proof ethanol) of 560 μL and a lysis buffer of 560 μL (buffer AVL, QIAGEN) were pre-loaded into their designated reservoirs 21a-21d (FIG. 7A) in the VLEAD buffer unit 21. The Zika virus sample was first loaded into the lysis buffer reservoir 21d (FIG. 9A) and discharged into the mixing unit 22 through sliding the buffer unit 21 to actuate the bearing ball valve (FIG. 9B), followed by the discharge of binding buffer 21c to mix with the virus lysate in the same manner. The detection unit 23 was further placed on a piece of blotting paper to filter the lysate through the laminated paper pad in the detection unit 23 (FIG. 9C). The paper pad functioned as a SPE material to enrich the Zika virus RNA from the lysate. The time cost by the blotting process depended on the type and volume of Zika sample used. The spiked samples tested by the inventors took no longer than 20 minutes to filter through the paper pad completely. The buffer unit 21 was further slid twice to discharge the two washing buffers 21b and 21a to purify the captured RNA (FIG. 9D).

After RNA enrichment, the buffer unit 21 and mixing unit 22 were separated from the detection unit 23. To detect the RNA captured, a piece of adhesive tape (Fellows©) was attached to the bottom to prevent amplification buffer leakage. A RT-LAMP amplification buffer of 25 μL was loaded to the detection unit 23, which was then sealed with another piece of adhesive tape on the top (FIG. 9E). The sealed detection unit 23 was incubated either in a travel mug (FIG. 13D) or in a water bath at 67° C. for 25 minutes in an Isotemp 105 water bath (ThermoFisher Scientific) for DNA amplification. To view the amplification result, 1 μL of 10,000× concentrate SYBR green I nucleic acid gel stain in DMSO (ThermoFisher Scientific) was added to the amplicons after incubation. An ULAKO blue LED flashlight (Amazon, WA, USA) powered by one AA battery was used to observe the green fluorescence from the positive samples (FIG. 9F).

Zika Virus Detection Using the VLEAD and the Ember™ Travel Mug

To incubate the detection unit 23 without having to use a standard power supply, the inventors chose to use a commercially available, battery powered coffee mug (FIG. 13D, Ember™ Travel Mug, Ember Technologies, Inc., Westlake Village, CA) which can heat water up to 62.5° C. and maintain the temperature for two hours once the rechargeable battery has been fully charged. The Ember™ mug also features adjustable temperature and real-time temperature display, which makes it suitable for incubating isothermal PCR such as the nucleic acid sequence-based amplification (NASBA) and LAMP. To verify the performance of Ember™ mug on RT-LAMP, the inventors purified Zika spiked water samples using the VLEAD apparatus 20, and submerged the VLEAD detection unit 23 directly into the water in the coffee mug after the maximum 62.5° C. had been reached. The detection unit 23 was incubated for 25 minutes before being taken out to check the amplification result.

Results and Discussions

Real-Time Zika Virus Detection

Figures 10A, 10B:
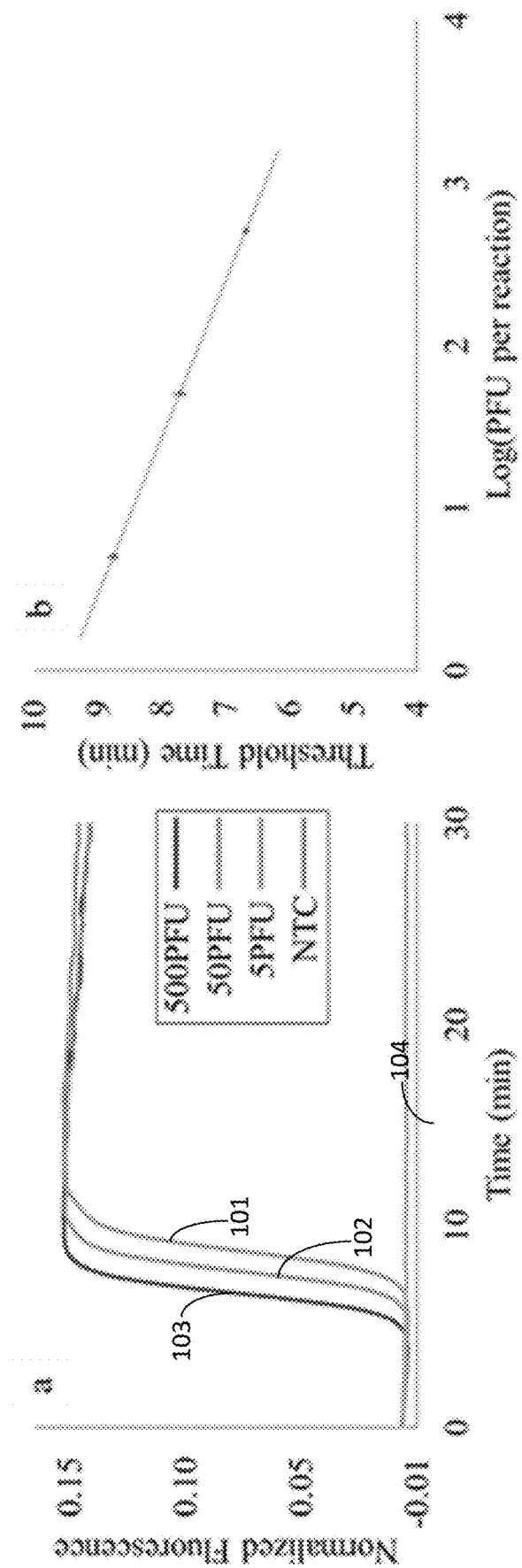
FIG. 10A depicts curves representing normalized fluorescent signals of 5, 50, and 500 PFU Zika virus genome equivalents amplification by RT-LAMP showing that all samples' amplification signals reached the plateau in 20 min.
FIG. 10B depicts a standard curve (log PFU per reaction vs. threshold time) generated with 3 replicates of each serial diluted Zika virus RNA samples.

FIG. 10A is a plot depicting curves 101-103 representing normalized fluorescent signals of 5, 50, and 500 PFU Zika virus genome equivalents amplification by RT-LAMP, respectively, showing that all samples' amplification signals reached the plateau in 15 min. Curve 104 represents NTC. FIG. 10B depicts a standard curve (log PFU per reaction vs. threshold time) generated with three replicates of each of the serial diluted Zika virus RNA samples. The QIAamp Viral RNA Mini Kit (QIAGEN) was used as a bench top standard to purify RNA from Zika virus spiked water. Fluorescence readings were taken from RT-LAMP containing 5, 50 and 500 PFU RNA equivalents using the QuantStudio 3 real-time PCR system (FIG. 10). All the positive wells were amplified within 15 minutes, and no non-specific amplification was observed during the 30-minute incubation period.

Zika Virus Detection Using the VLEAD

To evaluate the performance of the VLEAD to detect Zika virus in different kinds of aqueous sample, Zika virus was spiked in molecular-biology-grade water, humane urine, and human saliva. Each sample type with three or six duplicates were processed with the VLEAD apparatus 20 (FIGS. 7A-7D) to test its sensitivity. Its qualitative performance was also compared with bench top testing using the QIAamp Viral RNA mini kit (QIAGEN) and Zika virus spiked water (Table 3 below). In the bench top testing, the dilution factor of the elution buffer from the QIAGEN kit was taken into consideration to calculate the number of PFU Zika virus genome equivalents in each test.

TABLE 3

Zika virus detection using the VLEAD and bench top system.
The number of positive results/number of tests.

|  | Sample Type | 1 PFU | 0.5 PFU | 0.1 PFU | NTC |
|---|---|---|---|---|---|
| Device | Water | 3/3 | 3/3 | 3/3 | 0/3 |
|  | Urine | 3/3 | 3/3 | 1/3 | 0/4 |
|  | Saliva | 3/3 | 3/3 | 5/6 | 0/6 |
| Bench Top | Water | 3/3 | 3/3 | 1/3 | 0/3 |

NTC (no-template control)

Figures 11A, 11B, 11C:
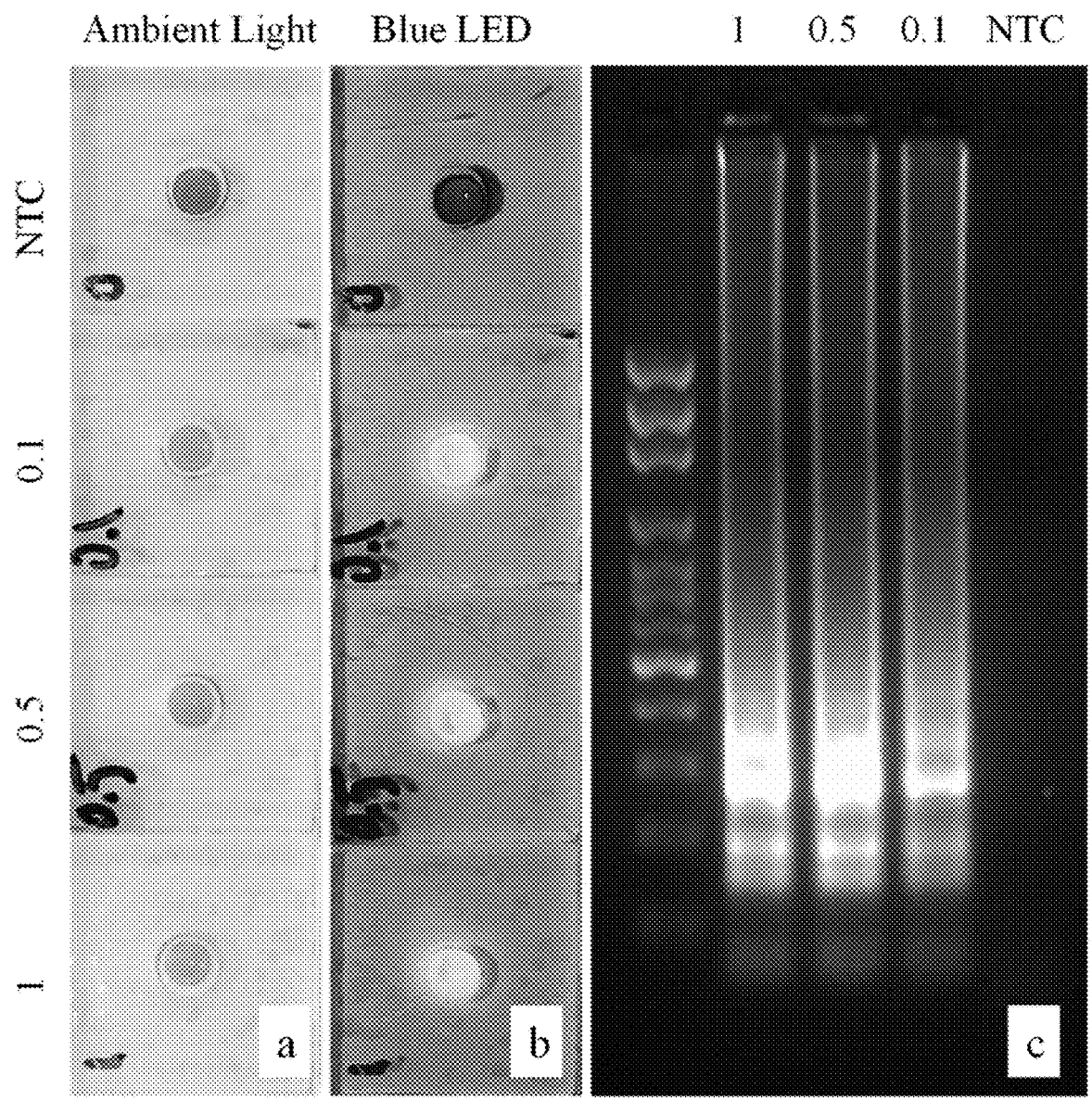
FIG. 11A is a photograph of the detection unit of the apparatus shown in FIGS. 7A-7D corresponding to the results under ambient light.
FIG. 11B is a photograph of the detection unit of the apparatus shown in FIGS. 7A-7D corresponding to the results under light from a blue LED flashlight.
FIG. 11C is a gel electrophoresis image of the amplicons from each device; from left lane to right: 100 bp DNA marker, 1, 0.5, 0.1 PFU and NTC.

FIGS. 11A-11C are photographs of the detection unit 23 corresponding to the results under the ambient light (FIG. 11A) and blue LED flashlight (FIG. 11B). The number of Zika virus in PFU spiked per device (1, 0.5, 0.1 PFU and NTC) labeled on the left of each device. FIG. 11C shows a gel electrophoresis image of the amplicons from each device. From left lane to right: 100 bp DNA marker, 1, 0.5, 0.1 PFU and NTC. The results shown in FIGS. 11A-11C indicate that the VLEAD apparatus 20 achieved comparable performance with the commercial QIAGEN kit, with 3/3 detected from 0.1 PFU Zika virus spiked water samples using the VLEAD apparatus 20 and method versus 1/3 detected using the QIAGEN kit. In the case of detecting Zika virus from body fluids such as urine and saliva, the impurities in those samples only affected the sensitivity slightly, with 1/3 0.1 PFU Zika spiked urine detected and 5/6 0.1 PFU Zika spiked saliva detected. Compared to bench top testing using the QIAGEN kit, the VLEAD apparatus 20 and method integrate all of the steps required for virus nucleic acid amplification test, from virus lysis, nucleic acid enrichment, purification, to amplification. As a result, there is no need to transfer RNA samples between different tubes, which greatly reduces the chance of sample contamination.

The RNA enrichment process of the VLEAD apparatus 20 is driven by the capillary forces generated by the laminated paper pad and blotting paper, thus eliminating the need to use lab equipment such as, for example, a centrifuge. Moreover, for an SPE approach using a spin column such as the QIAGEN kit, the RNA purified on the column needs to be eluted before downstream application. The elution step leads to sample dilution and comes with a "dead volume" absorbed on the column. In contrast, with the VLEAD apparatus 20 and method, all of the RNA purified on the paper pad could be used for nucleic acid amplification testing such as reverse transcription polymerase chain reactions (RT-PCR). It should also be noted that isothermal DNA amplification techniques other than LAMP, including strand displacement amplification (SDA) and helicase-dependent amplification (HDA), can also be used, as will be understood by those of skill in the art in view of the description provided herein.

To verify the detection result without lab instruments, the VLEAD method employed SYBR green to visualize the DNA amplicons through the green fluorescence excited by a handheld blue LED flashlight (FIG. 9F) from the DNA-dye-complex. Due to the high concentration of SYBR green required by naked-eye observation inhibiting the RT-LAMP enzymes, the dye was not included within the RT-LAMP buffer before the incubation step. Other known colorimetric approaches, such as, for example, those that use hydroxynaphthol blue, leuco crystal violet or phenol red, detect the by-products of RT-LAMP. These approaches often have less differences between the positive and negative results and therefore weren't incorporated into the VLEAD method of the representative embodiment.

Using the VLEAD apparatus 20, the inventors also tested a de-identified clinical urine sample collected from one Zika patient in Venezuela in 2016. The presence of Zika virus had been confirmed using plaque assay. The sample had been stored in a −80° C. freezer for two years before being tested using the VLEAD apparatus 20 and method. During the testing, the inventors observed slow filtration during the RNA enrichment step. As a result, the inventors reduced the sample volume to 100 μL to keep the blotting time around 20 minutes. A positive control of 10 PFU Zika virus spiked water and a negative control of DI water were made to validate the assay.

Figures 12A, 12B, 12C:
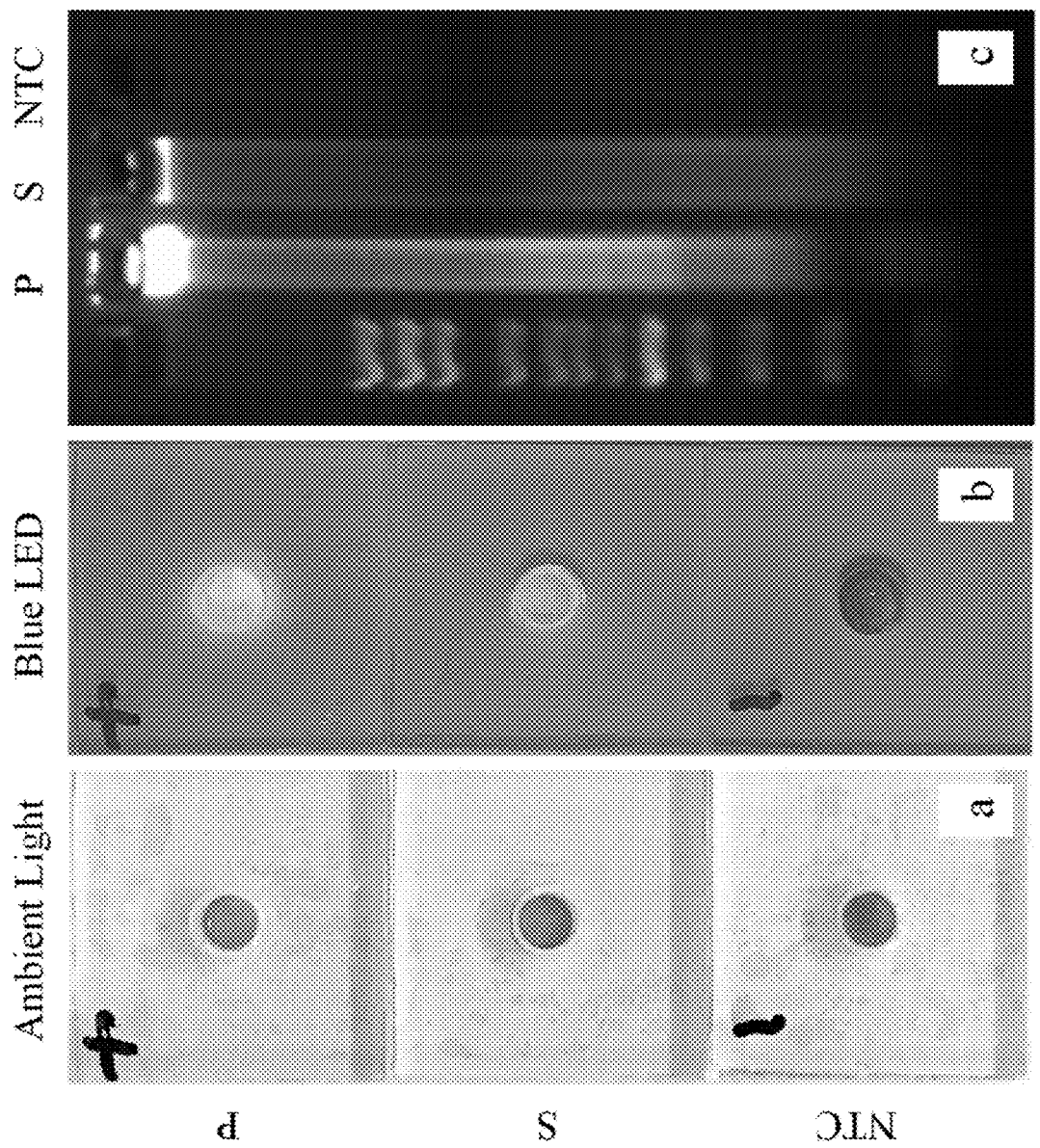
FIGS. 12A and 12B are photographs of the detection unit of the apparatus shown in FIGS. 7A-7D under ambient light and light from a blue LED flashlight, respectively; P is the positive control S is a clinical sample, and NTC is no-template control.
FIG. 12C is a gel electrophoresis image of the amplicons from each detection unit.

FIGS. 12A-12C are photographs of the detection unit 23 showing the test results. FIG. 12A is a photograph of the detection unit 23 under ambient light and FIG. 12B is a photograph of the detection unit 23 under a blue LED flashlight. FIG. 12C is a gel electrophoresis image of the amplicons from each device; from left lane to right: 100 bp DNA marker, positive control (P), clinical sample (S), and NTC. The presence of Zika virus was detected but the signal was somewhat weak, probably due to RNA degradation during the sample storage. The inventors repeated the experiment using two more aliquots from the same patient and were able to detect 2/3 of all the three aliquots.

The slow filtration observed in this testing could be caused by an increased amount of cell debris in the patient's urine related to disease progression or precipitations formed during the two-year storage. This issue is expected to be significantly less in fresh samples. Further it could potentially be solved by diluting the sample with water or digesting the sample with Proteinase K before sample loading.

Zika Virus Detection Using the VLEAD Apparatus and the Ember™ Travel Mug

Figures 13A, 13B, 13C, 13D:
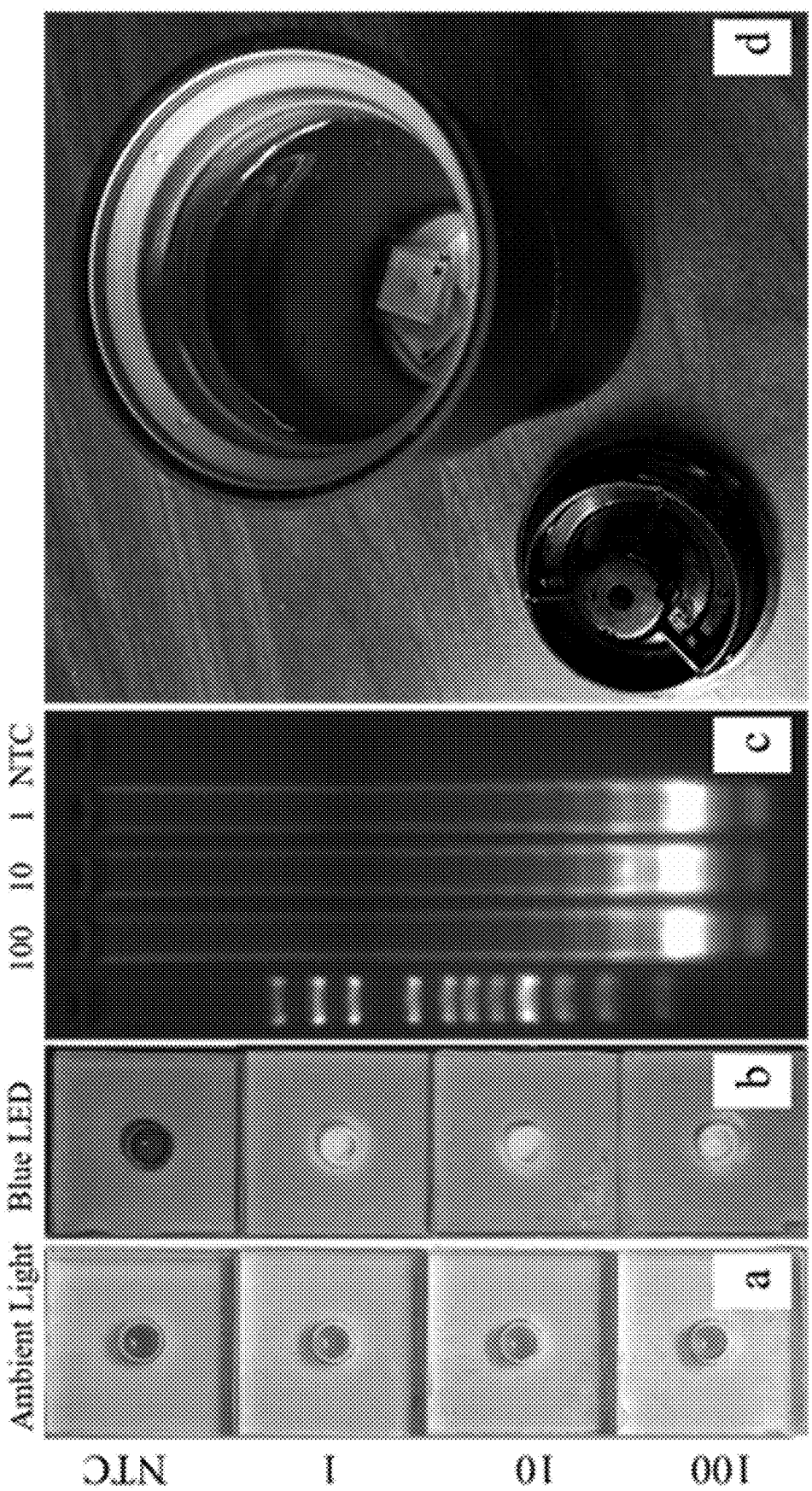
FIG. 13A is a photograph showing Zika virus detection using the detection unit of the apparatus shown in FIGS. 7A-7D incubated in the Ember™ travel mug and analyzed under ambient light.
FIG. 13B is a photograph showing Zika virus detection using the detection unit of the apparatus shown in FIGS. 7A-7D incubated in the Ember™ travel mug and analyzed under light from a blue LED flashlight.
FIG. 13C is a gel electrophoresis image of the amplicons from each detection unit; from left lane to right: 100 bp DNA marker, 100, 10, 1 PFU and NTC.
FIG. 13D is a photograph showing detection units submerged in water in an Ember™ travel mug.

Using the Ember™ travel mug as an incubator for RT-LAMP, the inventors successfully detected the 100, 10, and 1 PFU Zika RNA equivalents purified in the VLEAD apparatus 20 in 25 minutes (FIGS. 13A-13D). FIG. 13A is a photograph of the detection unit 23 under ambient light and FIG. 13B is a photograph of the detection unit 23 under a blue LED flashlight. FIG. 13C is a gel electrophoresis image of the amplicons from each device; from left lane to right: 100 bp DNA marker, positive control (P), clinical sample (S), and NTC. The cup shown in FIG. 13D has a volume capacity of 12 oz. which is more than enough volume to submerge the detection unit 23. The cup was filled close to the "MAX" line to reduce the temperature fluctuation upon adding the detection units 23 during the test. Even though the primer set that was used was optimized at 67° C., which is above the maximum temperature achievable by the Ember™ coffee mug without further customization, the LAMP method is sufficiently robust at a range of temperatures from 57° C. to 67° C.

Figure 14:
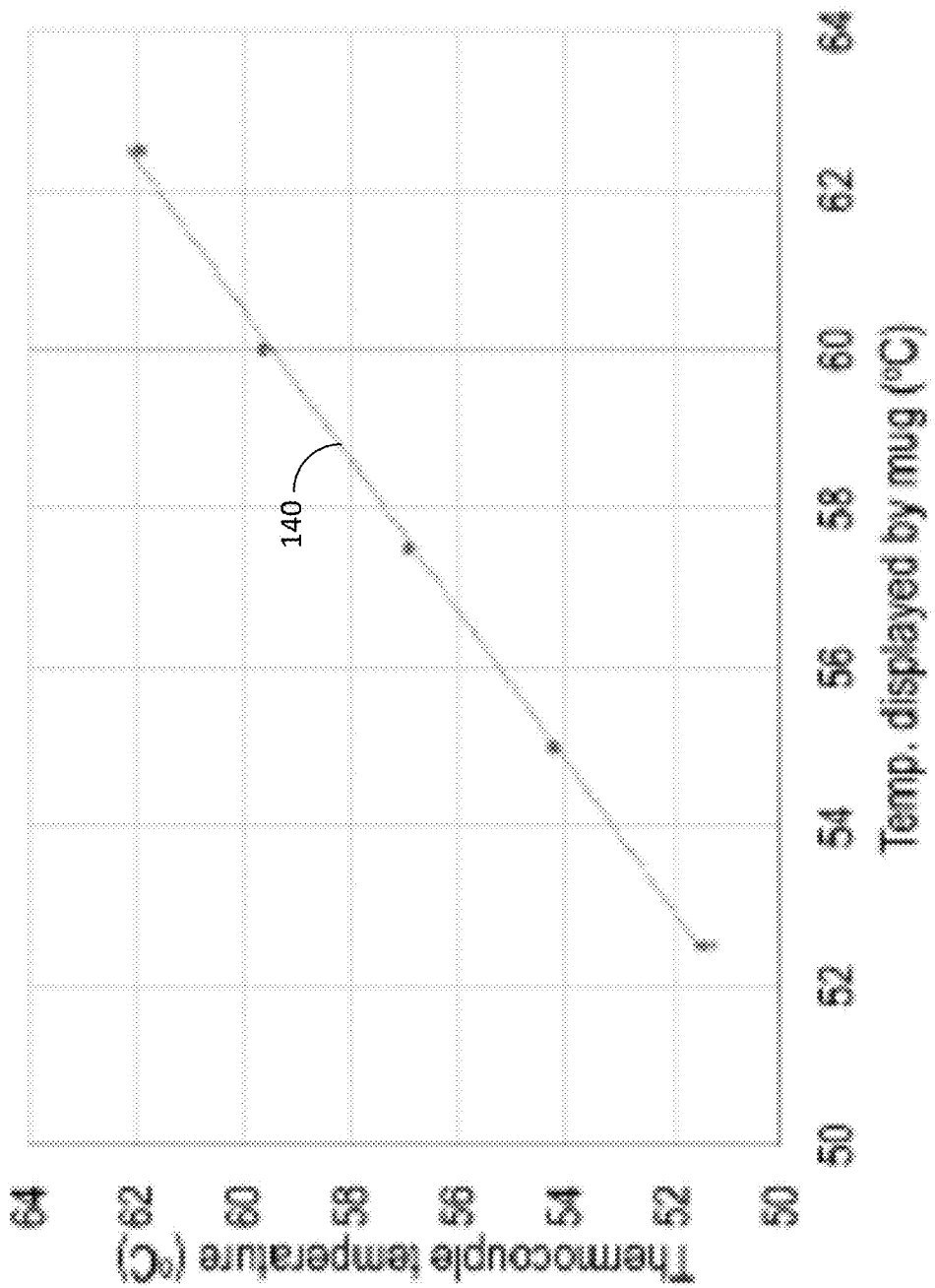
FIG. 14 is a plot of a temperature calibration curve 140 for calibrating the Ember™ mug shown in FIG. 13D.

FIG. 14 is a plot of a temperature calibration curve 140 for calibrating the Ember™ mug shown in FIG. 13D. Each data point on the curve 140 was measured three times with 5 min in between. The temperature of the Ember™ mug was first calibrated using a thermocouple which was inserted through a small opening in the lid designed for pressure release. The water temperature inside the mug was set and measured at 52.5° C., 55.0° C., 57.5° C., 60.0° C., and 62.5° C. Three measurements were taken for each temperature, with 1, 6, and 11 minutes after the temperature displayed by the Ember™ mug App had reached the set temperature.

Figures 15A, 15B:
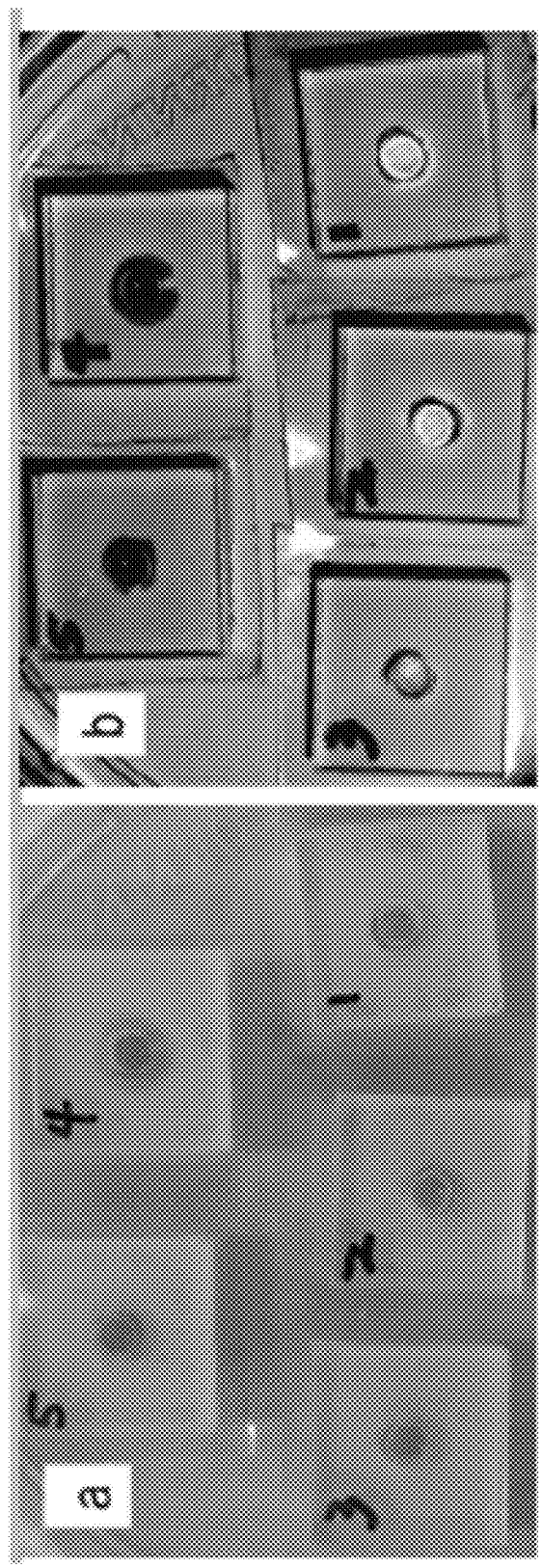
FIGS. 15A and 15B are photographs showing detection results under ambient light and blue LED flashlight, respectively, obtained by the apparatus 20 shown in FIGS. 7C and 9A-9F for detection of 14 µl of ZIKV-spiked urine samples.

Another advantage of using the apparatus 20 shown in FIGS. 7A-7D is that the detection limit in terms of the absolute amount of virus is not lowered as a result of increasing the volume of samples. FIGS. 15A and 15B are photographs showing detection results under ambient light and blue LED flashlight, respectively, obtained by the apparatus 20 shown in FIGS. 7C and 9A-9F for detection of 14 µl of ZIKV-spiked urine samples using the detection unit 23. Devices 1-4 shown in FIGS. 15A and 15B contain 10, 1, 0.5 and 0.1 PFU ZIKV, respectively. Device 5 functions as the negative control. This detection limit in terms of the absolute amount of virus, 0.5 PFU ZIKV per device, is the same as using 140 µl of ZIKV-spiked urine samples with state-of-the-art system discussed above in Table 3. However, the detection limit in terms of the virus concentration or "PFU per volume" is lowered by 10 times when a large volume of samples is used. The results also suggest that essentially all RNA molecules are captured by the paper pad of the detection unit.

Figure 16:
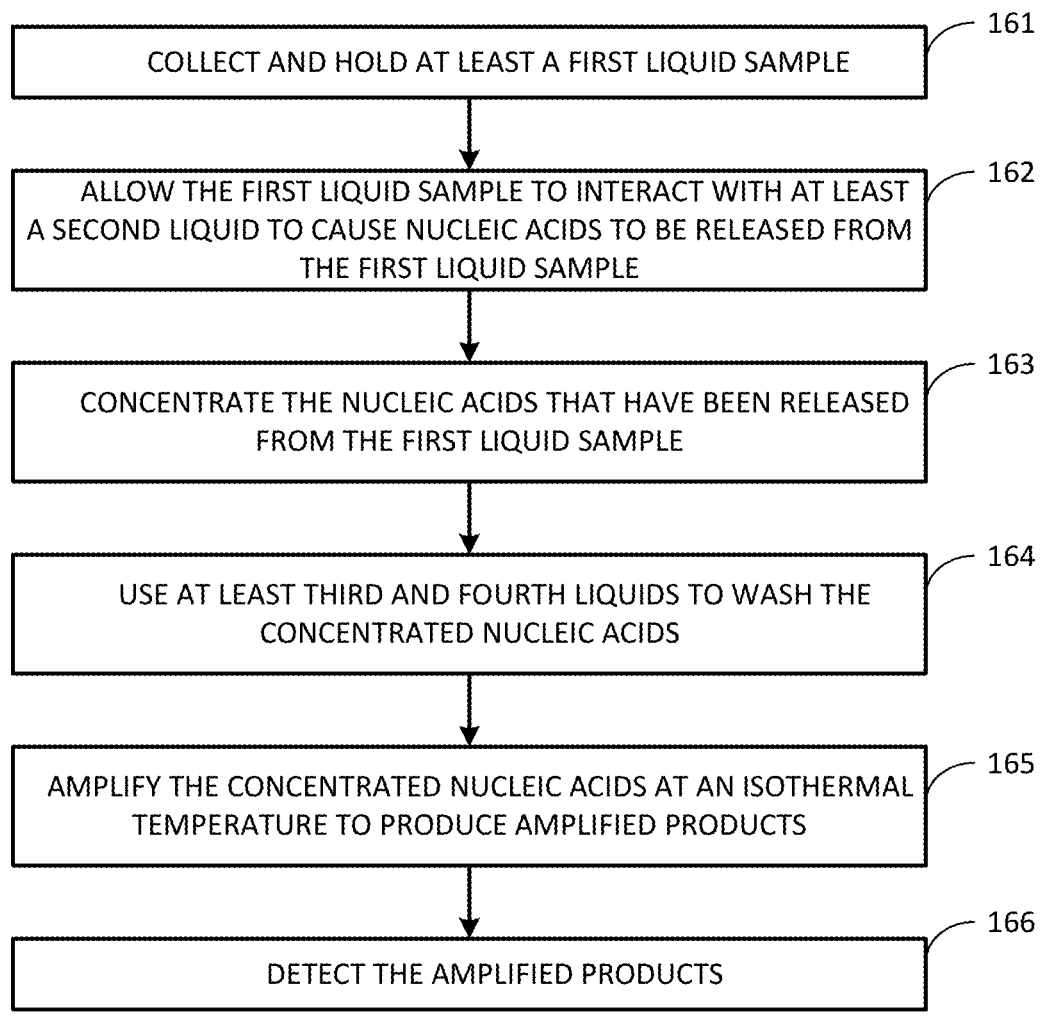
FIG. 16 is a flow diagram representing the method in accordance with a representative embodiment for preparing a sample for use in detecting microorganisms.

Another aspect of the inventive principles and concepts relates to a method for preparing a sample for use in detecting microorganisms. FIG. 16 is a flow diagram representing the method in accordance with a representative embodiment. Block 161 represents a step of collecting and holding at least a first liquid sample. Block 162 represents a step of allowing the first liquid sample to interact with at least a second liquid to cause nucleic acids to be released from the first liquid sample. Block 163 represents a step of concentrating nucleic acids that have been released from the first liquid sample. Block 164 represents a step of washing the concentrated nucleic acids using at least third and fourth liquids. Block 165 represents a step of amplifying the concentrated nucleic acids at an isothermal temperature to produce amplified products. Block 166 represents a step of detecting the amplified products.

It should be noted that some of the steps shown in FIG. 16 may be performed almost simultaneously rather than sequentially from one step to the next. It should also be noted that additional steps not explicitly shown in FIG. 16 may be included in the method and that modifications can be made to the steps shown in FIG. 16. Persons of skill in the art will understand, in view of the description provided herein.

Conclusions for The VLEAD Apparatus And Method

The VLEAD apparatus 20 and method achieve comparable sensitivity with a commercial SPE RNA extraction kit. Untreated cellulose has been used as a nucleic acid extraction material since the 1960s. However, its use in nucleic acid SPE is far less common nowadays compared to other materials such as silica[2] and chitosan. The mechanism of RNA absorption by cellulose fibers is also poorly understood due to lack of study. On the other hand, the VLEAD detection unit 23 made of laminated cellulose paper is uncomplicated, easy-to-use, of low cost and very sensitive in detecting RNA. The above results indicate that cellulose chromatography paper is a good alternative in developing platforms for nucleic acid extraction.

The VLEAD apparatus 20 was tested with human saliva and urine samples spiked with Zika virus. The disposable, 3D printed components allow the laminated paper pad to process a much larger sample volume (~100 µL) compared to traditional microfluidic paper-based analytical devices (less than 10 µL) and thus increase the sensitivity of the VLEAD apparatus 20. The VLEAD apparatus 20 was able to stably detect 0.5 PFU from Zika virus spiked urine and salvia and 0.1 PFU from Zika virus spiked water.

Thus, the VLEAD apparatus 20 and method can be used to perform an innovative and highly sensitive POC test for Zika virus and other viruses using paper and 3D printed materials. The VLEAD platform can also be used in detecting other microorganisms with different primers for RT-LAMP or other DNA amplification techniques.

Although the apparatuses 1 and 20 and corresponding methods have been demonstrated for two RNA viruses, they can be easily expanded into both DNA and RNA viruses. For DNA viruses, it will be even simpler since it does not need the reverse transcription step that transcripts RNA to DNA. Those of skill in the art will understand how the apparatuses 1 and 20 can be adapted for detecting bacteria, fungi, and other pathogens, which can be lysed to produce nucleic acids, followed by amplification and detection.

Results of Detecting SARS-CoV-2

RT-LAMP Reaction

The apparatus and method described above with reference to FIGS. 7A-7C were used to detect SARS-CoV-2. The detection results will now be described. Each 25-L RT-LAMP mix contains 2.5 µL of 10× isothermal amplification buffer, 8 U Bst 2.0 WarmStart® DNA polymerase, 7.5 U WarmStart® RTx reverse transcriptase, 2.5 µL of 10× concentrated primer mix, and a final concentration of 1.4 mM dNTPs and 6 mM MgSO$_4$. The 25-µL volume was filled up by nuclease-free water (not DEPC treated). Except for the nuclease-free water and dNTPs from ThermoFisher Scientific (MA, USA), the other reagents in the RT-LAMP mix were obtained from New England Biolabs (Ipswich, MA, USA). The 10× primer mix for SARS-CoV-2 contains 16 µM FIP/BIP, 2 µM F3/B3, and 8 µM LF/LB (Table 4 below). The primers were obtained from Integrated DNA Technologies (Coralville, Iowa, USA), and were chosen by following the literature.

For each 25-μL UDG RT-LAMP reaction mix, 0.5 units of Antarctic Thermolabile uracil-DNA glycosylase (UDG), and 0.7 mM of dUTP solution (New England Biolabs) were added to the RT-LAMP mix previously described, reducing the amount of nuclease-free water needed for the reaction.

TABLE 4

Sequences of RT-LAMP primers for SARS-COV-2 detection targeting the N gene. There are other RT-LAMP primers targeting N gene and other genes including ORF1a and S gene.

| Primer name | Primer sequence (5'-3') | Bases |
|---|---|---|
| F3 | TGGACCCCAAAATCAGCG | 18 |
| B3 | AGCCAATTTGGTCATCTGGA | 20 |
| FIP (F1c + F2) | CGTTGTTTTGATCGCGCCCC ATTACGTTTGGTGGAC CCTC | 40 |
| BIP (B1 + B2c) | ATACTGCGTCTTGGTTCACCGC ATTGGAACGCCTTG TCCTC | 41 |
| LF | TGCGTTCTCCATTCTGGTTACT | 22 |
| LB | TCTCACTCAACATGGCAAGGAA | 22 |

To assess the sensitivity of the RT-LAMP assay for detection of SARS-CoV-2, RNA was extracted from an isolate SARS CoV-2/human/USA/UF-1/2020 in VeroE6 cells.

The genome copy equivalents per microliter (GCEs/μL) of the extracted RNA was calculated using a standard curve on a rRT-PCR assay, which was determined to be $1 \times 10^6$ GCEs/μL. 10-fold serial dilutions were made using RNA storage solution (Invitrogen), and 1 μL of purified RNA of the different concentrations was added into 25-μL UDG RT-LAMP reactions, along with a non-template control. The RT-LAMP assay for SARS-CoV-2 detection showed high sensitivity with a low limit of detection of less than 10 GCEs.

Figures 17A, 17B, 17C, 17D:
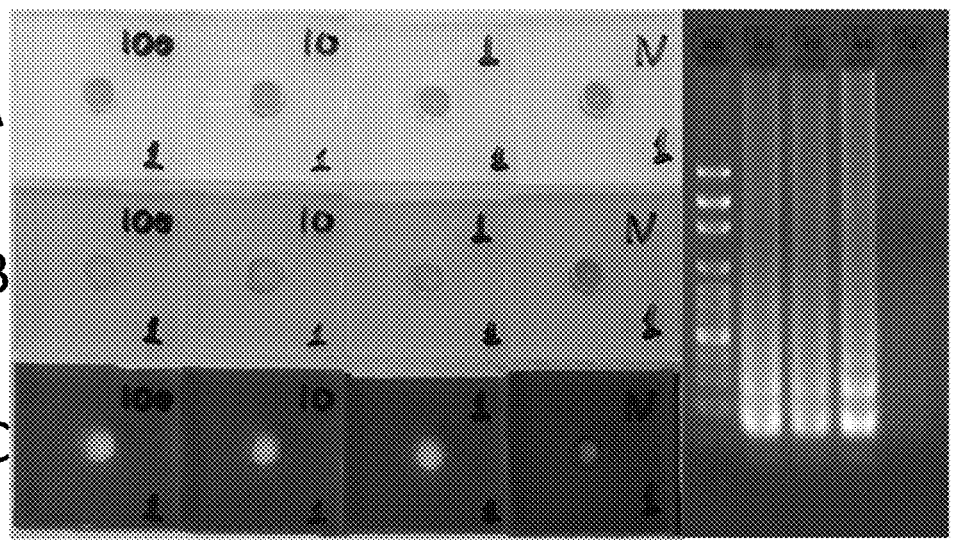
FIGS. 17A-17D are images depicting sensitivity tests for the SARS-CoV-2 RT-LAMP assay, incubating at 62.5° C.

The results were confirmed using gel electrophoresis and are shown in FIGS. 17A-17D. FIGS. 17A-17D are images depicting sensitivity tests for the SARS-CoV-2 RT-LAMP assay, incubating at 62.5° C. for 25 min. The tests demonstrated the ability to detect as low as a $10^6$ dilution of the purified SARS-CoV-2 RNA that was about $10^6$ GCE per microliter. Thus, the method and apparatus were able to detect less than 10 GCEs. From left to right, the units are in the following order: $10^4$ dilution, $10^5$ dilution, $10^6$ dilution, and a no template control. All of the concentrations were amplified after 25 minutes. FIG. 17A is photo taken under room lights; FIG. 17B is a photo taken under room lights and blue LED; FIG. 17C is a photo taken under blue LED with the room lights off, FIG. 17D shows confirmation of results by gel electrophoresis.

VARIOUS ASPECTS OF THE ABOVE-DESCRIBED INVENTIVE PRINCIPLES AND CONCEPTS

In accordance with one aspect, an apparatus for preparing a sample for use in detecting microorganisms is provided. The apparatus comprises a collector unit, a buffer unit, a mechanical coupling mechanism and a valve mechanism. The collector unit has at least a first reservoir for holding at least a first liquid sample. The buffer unit includes at least second, third and fourth reservoirs for holding at least second, third and fourth liquids, respectively. The mechanical coupling mechanism couples the collector unit and the buffer unit together in a manner that allows a user to create relative movement between the collector unit and the buffer unit by exerting a force on at least one of the buffer unit and the collector unit. The valve mechanism causes the second, third and fourth liquids to be released from the second, third and fourth reservoirs, respectively, into the first reservoir, in turn, when the user creates relative movement between the collector unit and the buffer unit to cause the second, third and fourth reservoirs to come into temporary alignment with the first reservoir for respective time periods.

In accordance with another aspect, the apparatus further comprises a detection unit removably coupled to the collector unit for detecting microorganisms. The detection unit receives liquid from the first reservoir and can be removed from the collector unit and analyzed to determine whether the liquid received by the detection unit contains a particular microorganism.

In accordance with another aspect, the collector unit is rotatably coupled to the buffer unit by the mechanical coupling mechanism such that the relative movement is created by the user exerting the force on the buffer unit to cause the buffer unit to rotate relative to the collector unit, thereby causing the second, third and fourth reservoirs to come into temporary alignment with the first reservoir for the respective time periods during which the second, third and fourth liquids are released, in turn, into the first reservoir.

In accordance with another aspect, the valve mechanism comprises a post, a first valve, a first ball, a second valve, a second ball, a third valve and a third ball. The post has a proximal end connected to a surface of the collector unit and a distal end opposite the proximal end. A first valve opening is disposed in a bottom of the second reservoir. The first ball is movably positioned in the first valve opening when the first valve opening is in a closed state. When the second reservoir is in temporary alignment with the first reservoir, the post comes into contact with the first ball to move the first ball away from the first valve opening to thereby place the first valve opening in an opened state. A second valve opening is disposed in a bottom of the third reservoir. The second ball is movably positioned in the second valve opening when the second valve opening is in a closed state. When the third reservoir is in temporary alignment with the first reservoir, the post comes into contact with the second ball to move the second ball away from the second valve opening to thereby place the second valve opening in an opened state. A third valve opening is disposed in a bottom of the fourth reservoir. The third ball is movably positioned in the third valve opening when the third valve opening is in a closed state. When the fourth reservoir is in temporary alignment with the first reservoir, the post comes into contact with the third ball to move the third ball away from the third valve opening to thereby place the third valve opening in an opened state.

In accordance with another aspect, the detection unit is a paper-based detection unit removably coupled to a bottom side of the collector unit. The first reservoir of the collector unit has an opening therein through which liquid held in the first reservoir passes and is received by the paper-based detection unit.

In accordance with another aspect, the paper-based detection unit is a laminated paper-based RNA amplification component.

In accordance with another aspect, the particular microorganism is a virus.

In accordance with another aspect, the virus is selected from the group comprising influenza virus, Zika virus, Dengue virus, Chikungunya virus, Ebola virus, hepatitis A virus, hepatitis B virus, hepatitis C virus, human immunodeficiency viruses (HIV) and Mayaro virus.

In accordance with another aspect, the particular microorganism is a bacterium.

In accordance with another aspect, the bacterium is selected from the group comprising *Escherichia coli* (*E. coli*), enterococci, Salmonellae, *Streptococcus pneumoniae*, *Staphylococcus aureus* and *Pseudomonas aeruginosa*.

In accordance with another aspect, the buffer unit further includes at least fifth reservoir for holding at least a fifth liquid. The valve mechanism causes the second, third, fourth and fifth liquids to be released from the second, third, fourth and fifth reservoirs, respectively, into the first reservoir, in turn, when the user creates relative movement between the collector unit and the buffer unit to cause the second, third, fourth and fifth reservoirs to come into temporary alignment with the first reservoir for respective time periods.

In accordance with another aspect, the valve mechanism further comprises a fourth valve opening disposed in a bottom of the fifth reservoir and a fourth ball movably positioned in the fourth valve opening when the fourth valve opening is in a closed state. When the fifth reservoir is in temporary alignment with the first reservoir, the post comes into contact with the fourth ball to move the fourth ball away from the fourth valve opening to thereby place the fourth valve opening in an opened state.

In accordance with another aspect, the collector unit and the buffer unit are slidably coupled to one another by the mechanical coupling mechanism such that when the user exerts the force on at least one of the buffer unit and the collector unit, one of the buffer unit and the collector unit slides relative to the other, thereby causing the second, third, fourth and fifth reservoirs to come into temporary alignment with the first reservoir for the respective time periods during which the second, third, fourth and fifth liquids are released, in turn, into the first reservoir. In accordance with another aspect, the detection unit is a paper-based detection unit removably coupled to a bottom side of the collector unit. The first reservoir of the collector unit has an opening therein through which liquid held in the first reservoir passes and is received by the paper-based detection unit. In accordance with another aspect, the paper-based detection unit is a laminated paper-based RNA amplification component.

In accordance with another aspect, a method is provided for preparing a sample to be used for detecting microorganisms. The method comprises placing a first liquid sample in at least a first reservoir of a collector unit of a microorganism detecting apparatus, placing at least second, third and fourth liquids in at least second, third and fourth reservoirs, respectively, of a buffer unit of the microorganism detecting apparatus, wherein the collector unit and the buffer unit are coupled together by a mechanical coupling mechanism in a manner that allows a user to create relative movement between the collector unit and the buffer unit by exerting a manual force on at least one of the buffer unit and the collector unit; and exerting the manual force on at least one of the buffer unit and the collector unit to create relative movement between the collector unit and the buffer unit to cause the second, third and fourth reservoirs to come into temporary alignment with the first reservoir for respective time periods, wherein a valve mechanism of the microorganism detecting apparatus causes the second, third and fourth liquids to be released from the second, third and fourth reservoirs, respectively, into the first reservoir, in turn, when the manual force is exerted to cause the second, third and fourth reservoirs to come into temporary alignment with the first reservoir for respective time periods.

In accordance with another aspect, the method further comprises, with a detection unit removably coupled to the collector unit, receiving liquid from the first reservoir, and removing the detection unit from the collector unit and analyzing the detection unit to determine whether the liquid received by the detection unit contains a particular microorganism.

In accordance with another aspect, a method is provided for preparing a sample for use in detecting microorganisms comprising, collecting and holding at least a first liquid sample, allowing the first liquid sample to interact with at least a second liquid to cause nucleic acids to be released from the first liquid sample, concentrating nucleic acids that have been released from the first liquid sample, washing the concentrated nucleic acids using at least third and fourth liquids, amplifying the concentrated nucleic acids at an isothermal temperature to produce amplified products, and detecting the amplified products.

It should be emphasized that the above-described embodiments are merely possible examples of implementations, merely set forth for a clear understanding of the inventive principles and concepts. For example, while the experiment was described with reference to platforms for detecting particular airborne and non-airborne viruses, other types of the apparatuses and methods described herein can be used to detect other types of airborne and non-airborne viruses and microorganisms. Many variations and modifications may be made to the above-described embodiments of the apparatuses 1 and 20 without departing from the scope of the disclosure. All such modifications and variations are intended to be included herein within the scope of this disclosure and the present invention.

What is claimed is:

1. An apparatus for preparing a sample for use in detecting microorganisms comprising:
   a collector unit having at least a first reservoir for holding at least a first liquid;
   a buffer unit including at least second, third and fourth reservoirs for holding at least second, third and fourth liquids, respectively, the collector unit and the buffer unit mechanically coupled together in a manner that allows a user to create relative movement between the collector unit and the buffer unit by exerting a force on the buffer unit, on the collector unit, or on both; and
   a valve mechanism that causes the second, third and fourth liquids to be released from the second, third and fourth reservoirs, respectively, into the first reservoir, in turn, when the user creates the relative movement between the collector unit and the buffer unit to cause the second, third and fourth reservoirs to come into temporary alignment with the first reservoir for respective time periods, the valve mechanism comprising:
   a post having a proximal end connected to a surface of the collector unit and a distal end opposite the proximal end;
   a first valve opening disposed in a bottom of the second reservoir;
   a first ball movably positioned in the first valve opening when the first valve opening is in a closed state, wherein when the second reservoir is in temporary alignment with the first reservoir, the post comes into contact with the first ball to move the first ball away from the first valve opening to thereby place the first valve opening in an opened state;
   a second valve opening disposed in a bottom of the third reservoir;
   a second ball movably positioned in the second valve opening when the second valve opening is in a closed state, wherein when the third reservoir is in temporary alignment with the first reservoir, the post comes into contact with the second ball to move the second ball away from the second valve opening to thereby place the second valve opening in an opened state;
   a third valve opening disposed in a bottom of the fourth reservoir; and
   a third ball movably positioned in the third valve opening when the third valve opening is in a closed state, wherein when the fourth reservoir is in temporary alignment with the first reservoir, the post comes into contact with the third ball to move the third ball away from the third valve opening to thereby place the third valve opening in an opened state.

2. The apparatus of claim 1, wherein the apparatus further comprises:
   a detection unit removably coupled to the collector unit, the detection unit receiving a liquid sample from the first reservoir, wherein the detection unit can be removed from the collector unit and analyzed to determine whether the liquid sample received by the detection unit contains a particular microorganism.

3. The apparatus of claim 2, wherein the collector unit is rotatably coupled to the buffer unit such that the relative movement is created by the user exerting the force on the buffer unit to cause the buffer unit to rotate relative to the collector unit, thereby causing the second, third and fourth reservoirs to come into temporary alignment with the first reservoir for the respective time periods during which the second, third and fourth liquids are released, in turn, into the first reservoir.

4. The apparatus of claim 2, wherein the detection unit is a paper-based detection unit removably coupled to a bottom side of the collector unit, the first reservoir of the collector unit having an opening therein through which the liquid sample passes and is received by the paper-based detection unit.

5. The apparatus of claim 4, wherein the paper-based detection unit is a laminated paper-based RNA amplification component.

6. The apparatus of claim 5, wherein the particular microorganism is a virus.

7. The apparatus of claim 6, wherein the virus is selected from the group consisting of influenza virus, Zika virus, Dengue virus, Chikungunya virus, Ebola virus, hepatitis A virus, hepatitis B virus, hepatitis C virus, human immunodeficiency viruses (HIV) and Mayaro virus.

8. The apparatus of claim 5, wherein the particular microorganism is a bacterium.

9. The apparatus of claim 7, wherein the bacterium is selected from the group consisting of *Escherichia coli* (*E. coli*), enterococci, Salmonellae, *Streptococcus pneumoniae, Staphylococcus aureus* and *Pseudomonas aeruginosa.*

10. The apparatus of claim 2, wherein the buffer unit further includes at least a fifth reservoir for holding at least a fifth liquid and wherein the valve mechanism causes the second, third, fourth and fifth liquids to be released from the second, third, fourth and fifth reservoirs, respectively, into the first reservoir, in turn, when the user creates relative movement between the collector unit and the buffer unit to cause the second, third, fourth and fifth reservoirs to come into temporary alignment with the first reservoir for respective time periods.

11. The apparatus of claim 10, wherein the valve mechanism further comprises:
a fourth valve opening disposed in a bottom of the fifth reservoir; and
a fourth ball movably positioned in the fourth valve opening when the fourth valve opening is in a closed state, wherein when the fifth reservoir is in temporary alignment with the first reservoir, the post comes into contact with the fourth ball to move the fourth ball away from the fourth valve opening to thereby place the fourth valve opening in an opened state.

12. The apparatus of claim 11, wherein the collector unit and the buffer unit are slidably coupled to one another such that when the user exerts the force on the buffer unit or the collector unit, one of the buffer unit and the collector unit slides relative to the other, thereby causing the second, third, fourth and fifth reservoirs to come into temporary alignment with the first reservoir for the respective time periods during which the second, third, fourth and fifth liquids are released, in turn, into the first reservoir.

13. The apparatus of claim 12, wherein the detection unit is a paper-based detection unit removably coupled to a bottom side of the collector unit, the first reservoir of the collector unit having an opening therein through which the liquid sample passes and is received by the paper-based detection unit.

14. The apparatus of claim 13, wherein the paper-based detection unit is a laminated paper-based RNA amplification component.

15. The apparatus of claim 14, wherein the particular microorganism is a virus selected from the group consisting of influenza virus, Zika virus, Dengue virus, Chikungunya virus, Ebola virus, hepatitis A virus, hepatitis B virus, hepatitis C virus, human immunodeficiency viruses (HIV) and Mayaro virus.

16. The apparatus of claim 14, wherein the particular microorganism is a bacterium selected from the group consisting of *Escherichia coli* (*E. coli*), enterococci, Salmonellae, *Streptococcus pneumoniae, Staphylococcus aureus* and *Pseudomonas aeruginosa.*

* * * * *

SEQUENCE LISTING

```
<160> NUMBER OF SEQ ID NOS: 77

<210> SEQ ID NO 1
<211> LENGTH: 22
<212> TYPE: DNA
<213> ORGANISM: Artificial sequence
<220> FEATURE:
<223> OTHER INFORMATION: Synthetic construct

<400> SEQUENCE: 1
accttctaga agacaagcat aa                                              22
```

<210> SEQ ID NO 2
<211> LENGTH: 14
<212> TYPE: DNA
<213> ORGANISM: Artificial sequence
<220> FEATURE:
<223> OTHER INFORMATION: Synthetic construct

<400> SEQUENCE: 2
tcctcataat cgat                                                          14

<210> SEQ ID NO 3
<211> LENGTH: 42
<212> TYPE: DNA
<213> ORGANISM: Artificial sequence
<220> FEATURE:
<223> OTHER INFORMATION: Synthetic construct

<400> SEQUENCE: 3
tggatttccc aggatccagc ggaaactatg caaactaaga gg                            42

<210> SEQ ID NO 4
<211> LENGTH: 38
<212> TYPE: DNA
<213> ORGANISM: Artificial sequence
<220> FEATURE:
<223> OTHER INFORMATION: Synthetic construct

<400> SEQUENCE: 4
tccacagcaa gctcatggtc tcctgggtaa cacgttcc                                 38

<210> SEQ ID NO 5
<211> LENGTH: 19
<212> TYPE: DNA
<213> ORGANISM: Artificial sequence
<220> FEATURE:
<223> OTHER INFORMATION: Synthetic construct

<400> SEQUENCE: 5
ccaaatgcaa tggggctac                                                     19

<210> SEQ ID NO 6
<211> LENGTH: 26
<212> TYPE: DNA
<213> ORGANISM: Artificial sequence
<220> FEATURE:
<223> OTHER INFORMATION: Synthetic construct

<400> SEQUENCE: 6
ctacattgtg gaaacatcta gttcag                                             26

<210> SEQ ID NO 7
<211> LENGTH: 20
<212> TYPE: DNA
<213> ORGANISM: Artificial sequence
<220> FEATURE:
<223> OTHER INFORMATION: Synthetic construct

<400> SEQUENCE: 7
agacgctttg tccaaaatgc                                                    20

<210> SEQ ID NO 8
<211> LENGTH: 20
<212> TYPE: DNA
<213> ORGANISM: Artificial sequence
<220> FEATURE:

<223> OTHER INFORMATION: Synthetic construct

<400> SEQUENCE: 8
tcacaagtgg cacacactag                                               20

<210> SEQ ID NO 9
<211> LENGTH: 40
<212> TYPE: DNA
<213> ORGANISM: Artificial sequence
<220> FEATURE:
<223> OTHER INFORMATION: Synthetic construct

<400> SEQUENCE: 9
ccttggcccc atggaacgtt atggggaccc gaacaacatg                         40

<210> SEQ ID NO 10
<211> LENGTH: 41
<212> TYPE: DNA
<213> ORGANISM: Artificial sequence
<220> FEATURE:
<223> OTHER INFORMATION: Synthetic construct

<400> SEQUENCE: 10
ttcaactggt gcacttgcca gtgtggtcac tgttcccatc c                       41

<210> SEQ ID NO 11
<211> LENGTH: 25
<212> TYPE: DNA
<213> ORGANISM: Artificial sequence
<220> FEATURE:
<223> OTHER INFORMATION: Synthetic construct

<400> SEQUENCE: 11
tgagcttctt gtatagttta actgc                                         25

<210> SEQ ID NO 12
<211> LENGTH: 22
<212> TYPE: DNA
<213> ORGANISM: Artificial sequence
<220> FEATURE:
<223> OTHER INFORMATION: Synthetic construct

<400> SEQUENCE: 12
tgcatgggcc tcatatacaa ca                                            22

<210> SEQ ID NO 13
<211> LENGTH: 19
<212> TYPE: DNA
<213> ORGANISM: Artificial sequence
<220> FEATURE:
<223> OTHER INFORMATION: Synthetic construct

<400> SEQUENCE: 13
aagctcagca aatcctaca                                                19

<210> SEQ ID NO 14
<211> LENGTH: 18
<212> TYPE: DNA
<213> ORGANISM: Artificial sequence
<220> FEATURE:
<223> OTHER INFORMATION: Synthetic construct

<400> SEQUENCE: 14
tccctcactt tgggtctt                                                 18

<210> SEQ ID NO 15
<211> LENGTH: 44
<212> TYPE: DNA
<213> ORGANISM: Artificial sequence
<220> FEATURE:
<223> OTHER INFORMATION: Synthetic construct

<400> SEQUENCE: 15
gactttgttg gtcagcacta gtagaaaagg gaaagaagtc ctcg        44

<210> SEQ ID NO 16
<211> LENGTH: 43
<212> TYPE: DNA
<213> ORGANISM: Artificial sequence
<220> FEATURE:
<223> OTHER INFORMATION: Synthetic construct

<400> SEQUENCE: 16
tctatcagaa tgcagatgca tatgttgcta tttccggctt gaa        43

<210> SEQ ID NO 17
<211> LENGTH: 20
<212> TYPE: DNA
<213> ORGANISM: Artificial sequence
<220> FEATURE:
<223> OTHER INFORMATION: Synthetic construct

<400> SEQUENCE: 17
gatggtgaat gccccatagc        20

<210> SEQ ID NO 18
<211> LENGTH: 24
<212> TYPE: DNA
<213> ORGANISM: Artificial sequence
<220> FEATURE:
<223> OTHER INFORMATION: Synthetic construct

<400> SEQUENCE: 18
ttttgtgggg tcatcaagat acag        24

<210> SEQ ID NO 19
<211> LENGTH: 19
<212> TYPE: DNA
<213> ORGANISM: Artificial sequence
<220> FEATURE:
<223> OTHER INFORMATION: Synthetic construct

<400> SEQUENCE: 19
aagctcagca aatcctaca        19

<210> SEQ ID NO 20
<211> LENGTH: 18
<212> TYPE: DNA
<213> ORGANISM: Artificial sequence
<220> FEATURE:
<223> OTHER INFORMATION: Synthetic construct

<400> SEQUENCE: 20
tccctcactt tgggtctt        18

<210> SEQ ID NO 21
<211> LENGTH: 48
<212> TYPE: DNA
<213> ORGANISM: Artificial sequence
<220> FEATURE:
<223> OTHER INFORMATION: Synthetic construct

<400> SEQUENCE: 21
gactttgttg gtcagcacta gtagatttta aagggaaaga agtcctcg        48

<210> SEQ ID NO 22
<211> LENGTH: 47
<212> TYPE: DNA
<213> ORGANISM: Artificial sequence
<220> FEATURE:
<223> OTHER INFORMATION: Synthetic construct

<400> SEQUENCE: 22
tctatcagaa tgcagatgca tatgttttt gctatttccg gcttgaa        47

<210> SEQ ID NO 23
<211> LENGTH: 20
<212> TYPE: DNA
<213> ORGANISM: Artificial sequence
<220> FEATURE:
<223> OTHER INFORMATION: Synthetic construct

<400> SEQUENCE: 23
gatggtgaat gccccatagc        20

<210> SEQ ID NO 24
<211> LENGTH: 23
<212> TYPE: DNA
<213> ORGANISM: Artificial sequence
<220> FEATURE:
<223> OTHER INFORMATION: Synthetic construct

<400> SEQUENCE: 24
ttgtggggtc atcaagatac agc        23

<210> SEQ ID NO 25
<211> LENGTH: 19
<212> TYPE: DNA
<213> ORGANISM: Artificial sequence
<220> FEATURE:
<223> OTHER INFORMATION: Synthetic construct

<400> SEQUENCE: 25
cagactaggc agatggtac        19

<210> SEQ ID NO 26
<211> LENGTH: 20
<212> TYPE: DNA
<213> ORGANISM: Artificial sequence
<220> FEATURE:
<223> OTHER INFORMATION: Synthetic construct

<400> SEQUENCE: 26
tcaggtgcaa gatcccaatg        20

<210> SEQ ID NO 27
<211> LENGTH: 49
<212> TYPE: DNA
<213> ORGANISM: Artificial sequence
<220> FEATURE:
<223> OTHER INFORMATION: Synthetic construct

<400> SEQUENCE: 27
gcctgcaaat tttcaagaag gtcttttgca atgagaacta ttgggactc        49

<210> SEQ ID NO 28
<211> LENGTH: 44

```
<212> TYPE: DNA
<213> ORGANISM: Artificial sequence
<220> FEATURE:
<223> OTHER INFORMATION: Synthetic construct

<400> SEQUENCE: 28
ccagaagcga atgggagtgc ttttatttgc tgcaatgacg agag         44

<210> SEQ ID NO 29
<211> LENGTH: 20
<212> TYPE: DNA
<213> ORGANISM: Artificial sequence
<220> FEATURE:
<223> OTHER INFORMATION: Synthetic construct

<400> SEQUENCE: 29
agaccagcac tggagctagg                                    20

<210> SEQ ID NO 30
<211> LENGTH: 21
<212> TYPE: DNA
<213> ORGANISM: Artificial sequence
<220> FEATURE:
<223> OTHER INFORMATION: Synthetic construct

<400> SEQUENCE: 30
gatgcagcga ttcaagtgat c                                  21

<210> SEQ ID NO 31
<211> LENGTH: 21
<212> TYPE: DNA
<213> ORGANISM: Artificial sequence
<220> FEATURE:
<223> OTHER INFORMATION: Synthetic construct

<400> SEQUENCE: 31
ccgggagaca aataacatt c                                   21

<210> SEQ ID NO 32
<211> LENGTH: 21
<212> TYPE: DNA
<213> ORGANISM: Artificial sequence
<220> FEATURE:
<223> OTHER INFORMATION: Synthetic construct

<400> SEQUENCE: 32
gtatattctg aaatgggagg c                                  21

<210> SEQ ID NO 33
<211> LENGTH: 45
<212> TYPE: DNA
<213> ORGANISM: Artificial sequence
<220> FEATURE:
<223> OTHER INFORMATION: Synthetic construct

<400> SEQUENCE: 33
cagatccagc atttctttcc attggaagca actggaaatc tagtg         45

<210> SEQ ID NO 34
<211> LENGTH: 45
<212> TYPE: DNA
<213> ORGANISM: Artificial sequence
<220> FEATURE:
<223> OTHER INFORMATION: Synthetic construct

<400> SEQUENCE: 34
```
tatcatttca gatacaccag tccactggtg tttatagcac ccttg         45

<210> SEQ ID NO 35
<211> LENGTH: 19
<212> TYPE: DNA
<213> ORGANISM: Artificial sequence
<220> FEATURE:
<223> OTHER INFORMATION: Synthetic construct

<400> SEQUENCE: 35
cgaatgcata tctcggtac         19

<210> SEQ ID NO 36
<211> LENGTH: 19
<212> TYPE: DNA
<213> ORGANISM: Artificial sequence
<220> FEATURE:
<223> OTHER INFORMATION: Synthetic construct

<400> SEQUENCE: 36
atacaacttg tcaaacacc         19

<210> SEQ ID NO 37
<211> LENGTH: 18
<212> TYPE: DNA
<213> ORGANISM: Artificial sequence
<220> FEATURE:
<223> OTHER INFORMATION: Synthetic construct

<400> SEQUENCE: 37
ttgtcaggct cctgtcaa         18

<210> SEQ ID NO 38
<211> LENGTH: 20
<212> TYPE: DNA
<213> ORGANISM: Artificial sequence
<220> FEATURE:
<223> OTHER INFORMATION: Synthetic construct

<400> SEQUENCE: 38
ttgctacgaa ccttgttgat         20

<210> SEQ ID NO 39
<211> LENGTH: 41
<212> TYPE: DNA
<213> ORGANISM: Artificial sequence
<220> FEATURE:
<223> OTHER INFORMATION: Synthetic construct

<400> SEQUENCE: 39
tggcacccta gtgtccactt tttaggaata gccatgaccg a         41

<210> SEQ ID NO 40
<211> LENGTH: 41
<212> TYPE: DNA
<213> ORGANISM: Artificial sequence
<220> FEATURE:
<223> OTHER INFORMATION: Synthetic construct

<400> SEQUENCE: 40
caagaaggca ctcgtcaggt tttgtgtttg cctagctctt t         41

<210> SEQ ID NO 41
<211> LENGTH: 18
<212> TYPE: DNA
<213> ORGANISM: Artificial sequence -continued
<220> FEATURE:
<223> OTHER INFORMATION: Synthetic construct

<400> SEQUENCE: 41
tgctgaccat acggtgtg                                                   18

<210> SEQ ID NO 42
<211> LENGTH: 19
<212> TYPE: DNA
<213> ORGANISM: Artificial sequence
<220> FEATURE:
<223> OTHER INFORMATION: Synthetic construct

<400> SEQUENCE: 42
ggtctcttcc tggttgtgg                                                  19

<210> SEQ ID NO 43
<211> LENGTH: 18
<212> TYPE: DNA
<213> ORGANISM: Artificial sequence
<220> FEATURE:
<223> OTHER INFORMATION: Synthetic construct

<400> SEQUENCE: 43
cagttcacac ggcccttg                                                   18

<210> SEQ ID NO 44
<211> LENGTH: 20
<212> TYPE: DNA
<213> ORGANISM: Artificial sequence
<220> FEATURE:
<223> OTHER INFORMATION: Synthetic construct

<400> SEQUENCE: 44
tgtacctcca ctgtgactgt                                                 20

<210> SEQ ID NO 45
<211> LENGTH: 40
<212> TYPE: DNA
<213> ORGANISM: Artificial sequence
<220> FEATURE:
<223> OTHER INFORMATION: Synthetic construct

<400> SEQUENCE: 45
ggcgacattt caagtggcca gagagctcta gaggctgaga                           40

<210> SEQ ID NO 46
<211> LENGTH: 41
<212> TYPE: DNA
<213> ORGANISM: Artificial sequence
<220> FEATURE:
<223> OTHER INFORMATION: Synthetic construct

<400> SEQUENCE: 46
agggcgtgtc atactccttg tgagtgtttc agccgggatc t                         41

<210> SEQ ID NO 47
<211> LENGTH: 20
<212> TYPE: DNA
<213> ORGANISM: Artificial sequence
<220> FEATURE:
<223> OTHER INFORMATION: Synthetic construct

<400> SEQUENCE: 47
ccttcccttt gcaccatcca                                                 20

```
<210> SEQ ID NO 48
<211> LENGTH: 20
<212> TYPE: DNA
<213> ORGANISM: Artificial sequence
<220> FEATURE:
<223> OTHER INFORMATION: Synthetic construct

<400> SEQUENCE: 48
taccgcagcg ttcacattca                                                 20

<210> SEQ ID NO 49
<211> LENGTH: 19
<212> TYPE: DNA
<213> ORGANISM: Artificial sequence
<220> FEATURE:
<223> OTHER INFORMATION: Synthetic construct

<400> SEQUENCE: 49
tggagggaca ggtacaagt                                                  19

<210> SEQ ID NO 50
<211> LENGTH: 19
<212> TYPE: DNA
<213> ORGANISM: Artificial sequence
<220> FEATURE:
<223> OTHER INFORMATION: Synthetic construct

<400> SEQUENCE: 50
tgtggacctc tccacatgg                                                  19

<210> SEQ ID NO 51
<211> LENGTH: 40
<212> TYPE: DNA
<213> ORGANISM: Artificial sequence
<220> FEATURE:
<223> OTHER INFORMATION: Synthetic construct

<400> SEQUENCE: 51
cgcagatacc atcttcccag gcatcctgac tcccccgta                            40

<210> SEQ ID NO 52
<211> LENGTH: 39
<212> TYPE: DNA
<213> ORGANISM: Artificial sequence
<220> FEATURE:
<223> OTHER INFORMATION: Synthetic construct

<400> SEQUENCE: 52
aaggggagct caacgcaatc cgatcccaca acgaccgtc                            39

<210> SEQ ID NO 53
<211> LENGTH: 18
<212> TYPE: DNA
<213> ORGANISM: Artificial sequence
<220> FEATURE:
<223> OTHER INFORMATION: Synthetic construct

<400> SEQUENCE: 53
tgcttgactg ctgctgcc                                                   18

<210> SEQ ID NO 54
<211> LENGTH: 19
<212> TYPE: DNA
<213> ORGANISM: Artificial sequence
<220> FEATURE:
<223> OTHER INFORMATION: Synthetic construct
```

```
<400> SEQUENCE: 54
tgacatccca ttgccttgg                                                      19

<210> SEQ ID NO 55
<211> LENGTH: 20
<212> TYPE: DNA
<213> ORGANISM: Artificial sequence
<220> FEATURE:
<223> OTHER INFORMATION: Synthetic construct

<400> SEQUENCE: 55
cttccctttg caccatccat                                                     20

<210> SEQ ID NO 56
<211> LENGTH: 40
<212> TYPE: DNA
<213> ORGANISM: Artificial sequence
<220> FEATURE:
<223> OTHER INFORMATION: Synthetic construct

<400> SEQUENCE: 56
ggcgtgggca tccttgaatt ctgcagacac cggaactcca                               40

<210> SEQ ID NO 57
<211> LENGTH: 40
<212> TYPE: DNA
<213> ORGANISM: Artificial sequence
<220> FEATURE:
<223> OTHER INFORMATION: Synthetic construct

<400> SEQUENCE: 57
ggcaaaccgt cgtcgttctg gctcagcctc tagagctcca                               40

<210> SEQ ID NO 58
<211> LENGTH: 21
<212> TYPE: DNA
<213> ORGANISM: Artificial sequence
<220> FEATURE:
<223> OTHER INFORMATION: Synthetic construct

<400> SEQUENCE: 58
tgcctctttg ttgttccagt g                                                   21

<210> SEQ ID NO 59
<211> LENGTH: 17
<212> TYPE: DNA
<213> ORGANISM: Artificial sequence
<220> FEATURE:
<223> OTHER INFORMATION: Synthetic construct

<400> SEQUENCE: 59
agccgttcac acggctc                                                        17

<210> SEQ ID NO 60
<211> LENGTH: 20
<212> TYPE: DNA
<213> ORGANISM: Artificial sequence
<220> FEATURE:
<223> OTHER INFORMATION: Synthetic construct

<400> SEQUENCE: 60
cggatgggat aggctcaaac                                                     20

<210> SEQ ID NO 61
```

<211> LENGTH: 18
<212> TYPE: DNA
<213> ORGANISM: Artificial sequence
<220> FEATURE:
<223> OTHER INFORMATION: Synthetic construct

<400> SEQUENCE: 61
atggacctcc cgtccttg                                                    18

<210> SEQ ID NO 62
<211> LENGTH: 42
<212> TYPE: DNA
<213> ORGANISM: Artificial sequence
<220> FEATURE:
<223> OTHER INFORMATION: Synthetic construct

<400> SEQUENCE: 62
cctgagggca tgtgcaaacc tagaatggca gtcagtggag at                         42

<210> SEQ ID NO 63
<211> LENGTH: 42
<212> TYPE: DNA
<213> ORGANISM: Artificial sequence
<220> FEATURE:
<223> OTHER INFORMATION: Synthetic construct

<400> SEQUENCE: 63
accctcaact ggatgggaca actggagctt gttgaagtgg tg                         42

<210> SEQ ID NO 64
<211> LENGTH: 21
<212> TYPE: DNA
<213> ORGANISM: Artificial sequence
<220> FEATURE:
<223> OTHER INFORMATION: Synthetic construct

<400> SEQUENCE: 64
catcaattgg cttcacaacg c                                                21

<210> SEQ ID NO 65
<211> LENGTH: 22
<212> TYPE: DNA
<213> ORGANISM: Artificial sequence
<220> FEATURE:
<223> OTHER INFORMATION: Synthetic construct

<400> SEQUENCE: 65
gggaagaagt tccgttttgc tc                                               22

<210> SEQ ID NO 66
<211> LENGTH: 18
<212> TYPE: DNA
<213> ORGANISM: Artificial sequence
<220> FEATURE:
<223> OTHER INFORMATION: Synthetic construct

<400> SEQUENCE: 66
gacttctgct gggtcatg                                                    18

<210> SEQ ID NO 67
<211> LENGTH: 19
<212> TYPE: DNA
<213> ORGANISM: Artificial sequence
<220> FEATURE:
<223> OTHER INFORMATION: Synthetic construct

<400> SEQUENCE: 67

```
gccaacaatt ccgacacta                                              19
```

<210> SEQ ID NO 68
<211> LENGTH: 40
<212> TYPE: DNA
<213> ORGANISM: Artificial sequence
<220> FEATURE:
<223> OTHER INFORMATION: Synthetic construct

<400> SEQUENCE: 68

```
ccccactgaa ccccatctat tgggtcttgg cgattctagc                       40
```

<210> SEQ ID NO 69
<211> LENGTH: 42
<212> TYPE: DNA
<213> ORGANISM: Artificial sequence
<220> FEATURE:
<223> OTHER INFORMATION: Synthetic construct

<400> SEQUENCE: 69

```
gttcaagaaa gatctggctg cccctcgtct tcttcttctc ct                    42
```

<210> SEQ ID NO 70
<211> LENGTH: 20
<212> TYPE: DNA
<213> ORGANISM: Artificial sequence
<220> FEATURE:
<223> OTHER INFORMATION: Synthetic construct

<400> SEQUENCE: 70

```
gcttgattgc cgtgaatctc                                             20
```

<210> SEQ ID NO 71
<211> LENGTH: 22
<212> TYPE: DNA
<213> ORGANISM: Artificial sequence
<220> FEATURE:
<223> OTHER INFORMATION: Synthetic construct

<400> SEQUENCE: 71

```
gctgagaata atcaatgcca gg                                          22
```

<210> SEQ ID NO 72
<211> LENGTH: 18
<212> TYPE: DNA
<213> ORGANISM: Artificial sequence
<220> FEATURE:
<223> OTHER INFORMATION: Synthetic construct

<400> SEQUENCE: 72

```
tggaccccaa aatcagcg                                               18
```

<210> SEQ ID NO 73
<211> LENGTH: 20
<212> TYPE: DNA
<213> ORGANISM: Artificial sequence
<220> FEATURE:
<223> OTHER INFORMATION: Synthetic construct

<400> SEQUENCE: 73

```
agccaatttg gtcatctgga                                             20
```

<210> SEQ ID NO 74
<211> LENGTH: 40
<212> TYPE: DNA

```
<213> ORGANISM: Artificial sequence
<220> FEATURE:
<223> OTHER INFORMATION: Synthetic construct

<400> SEQUENCE: 74
cgttgttttg atcgcgcccc attacgtttg gtggaccctc                              40

<210> SEQ ID NO 75
<211> LENGTH: 41
<212> TYPE: DNA
<213> ORGANISM: Artificial sequence
<220> FEATURE:
<223> OTHER INFORMATION: Synthetic construct

<400> SEQUENCE: 75
atactgcgtc ttggttcacc gcattggaac gccttgtcct c                           41

<210> SEQ ID NO 76
<211> LENGTH: 22
<212> TYPE: DNA
<213> ORGANISM: Artificial sequence
<220> FEATURE:
<223> OTHER INFORMATION: Synthetic construct

<400> SEQUENCE: 76
tgcgttctcc attctggtta ct                                                22

<210> SEQ ID NO 77
<211> LENGTH: 22
<212> TYPE: DNA
<213> ORGANISM: Artificial sequence
<220> FEATURE:
<223> OTHER INFORMATION: Synthetic construct

<400> SEQUENCE: 77
tctcactcaa catggcaagg aa                                                22
```